US011229551B2

(12) United States Patent
Bergt et al.

(10) Patent No.: US 11,229,551 B2
(45) Date of Patent: Jan. 25, 2022

(54) OPTHALMOLOGICAL THERAPY SYSTEM AND METHOD FOR PROCESSING A PORTION OF A PROCESSING VOLUME OF A TRANSPARENT MATERIAL BY APPLICATION OF FOCUSED RADIATION

(71) Applicant: Carl Zeiss Meditec AG, Jena (DE)

(72) Inventors: Michael Bergt, Weimar (DE); Thomas Hamann, Jena (DE); Robert Pomraenke, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 510 days.

(21) Appl. No.: 15/742,233

(22) PCT Filed: Jul. 6, 2016

(86) PCT No.: PCT/EP2016/066033
§ 371 (c)(1),
(2) Date: Jan. 5, 2018

(87) PCT Pub. No.: WO2017/005815
PCT Pub. Date: Jan. 12, 2017

(65) Prior Publication Data
US 2018/0193196 A1    Jul. 12, 2018

(30) Foreign Application Priority Data

Jul. 9, 2015 (DE) .................. 10 2015 2121 877.6

(51) Int. Cl.
*A61F 9/00* (2006.01)
*A61F 9/008* (2006.01)

(52) U.S. Cl.
CPC ...... *A61F 9/00834* (2013.01); *A61F 9/00817* (2013.01); *A61F 9/00821* (2013.01);
(Continued)

(58) Field of Classification Search
CPC .. A61F 2009/00897; A61F 2009/00846; A61F 2009/0087; A61F 2009/00872;
(Continued)

(56) References Cited

U.S. PATENT DOCUMENTS 5,984,916 A    11/1999 Lai
7,621,637 B2 *  11/2009 Rathjen ................... A61F 9/008
                                                                    351/221
(Continued)

FOREIGN PATENT DOCUMENTS

DE    10 2011 085 047 A1    4/2013
DE    10 2011 085046 A1     4/2013
(Continued)

OTHER PUBLICATIONS

PCT International Search Report and Written Opinion for International Application No. PCT/EP2016/066033, dated Jul. 6, 2016, 14 pages.
(Continued)

Primary Examiner — Rex R Holmes
Assistant Examiner — Sana Sahand
(74) Attorney, Agent, or Firm — Patterson Thuente Pedersen, P.A.

(57) ABSTRACT

A system for processing a portion in a processing volume of a transparent material by application of focused radiation including a device for generating and an optical system for focusing radiation, with a device for changing the position of the focus of the radiation and a control device. This system performs a slow scanning movement of the focus and an independent fast scanning movement of the focus which section can be moved by the slow scanning movement in the entire processing volume in an arbitrary direction; as well as by a system into which a scan pattern is encoded, with scanning movement including at least one lateral base
(Continued)

component in the x- and/or y-direction, which is superimposed by components with synchronous change-of-direction-movements in the z-direction and in x-direction and/or y-direction. The invention also includes corresponding methods, a control program product and a planning unit.

22 Claims, 18 Drawing Sheets

(52) U.S. Cl.
CPC .. *A61F 9/00825* (2013.01); *A61F 2009/0087* (2013.01); *A61F 2009/00846* (2013.01); *A61F 2009/00872* (2013.01); *A61F 2009/00874* (2013.01); *A61F 2009/00897* (2013.01)

(58) Field of Classification Search
CPC ........ A61F 2009/00874; A61F 9/00825; A61F 9/00834; A61F 9/00817; A61F 9/00821
USPC .......................................................... 606/4–6
See application file for complete search history.

(56) References Cited

U.S. PATENT DOCUMENTS

| | | | | |
|---|---|---|---|---|
| 2007/0293851 | A1* | 12/2007 | Muhlhoff | A61F 9/008 606/11 |
| 2008/0077121 | A1* | 3/2008 | Rathjen | A61F 9/008 606/5 |
| 2011/0028955 | A1* | 2/2011 | Raksi | A61F 9/008 606/4 |
| 2012/0029491 | A1* | 2/2012 | Rathjen | A61F 9/008 606/4 |
| 2012/0029492 | A1* | 2/2012 | Rathjen | A61F 9/00827 606/5 |
| 2014/0276674 | A1* | 9/2014 | Lee | A61F 9/008 606/4 |

FOREIGN PATENT DOCUMENTS

| | | |
|---|---|---|
| EP | 2 412 341 A1 | 2/2012 |
| EP | 2 596 773 B1 | 5/2013 |
| WO | WO 2013/057318 A1 | 4/2013 |
| WO | WO 2016/050779 A1 | 4/2016 |

OTHER PUBLICATIONS

English translation of PCT International Search Report for International Application No. PCT/EP2016/066033, dated Jul. 6, 2016, 2 pages.

DE Search Report for 10 2015 212 877,6, dated Aug. 4, 2016, 16 pages.

PCT International Preliminary Report on Patentability for International Application No. PCT/EP2016/066033, dated Jan. 18, 2018, 10 pages.

* cited by examiner

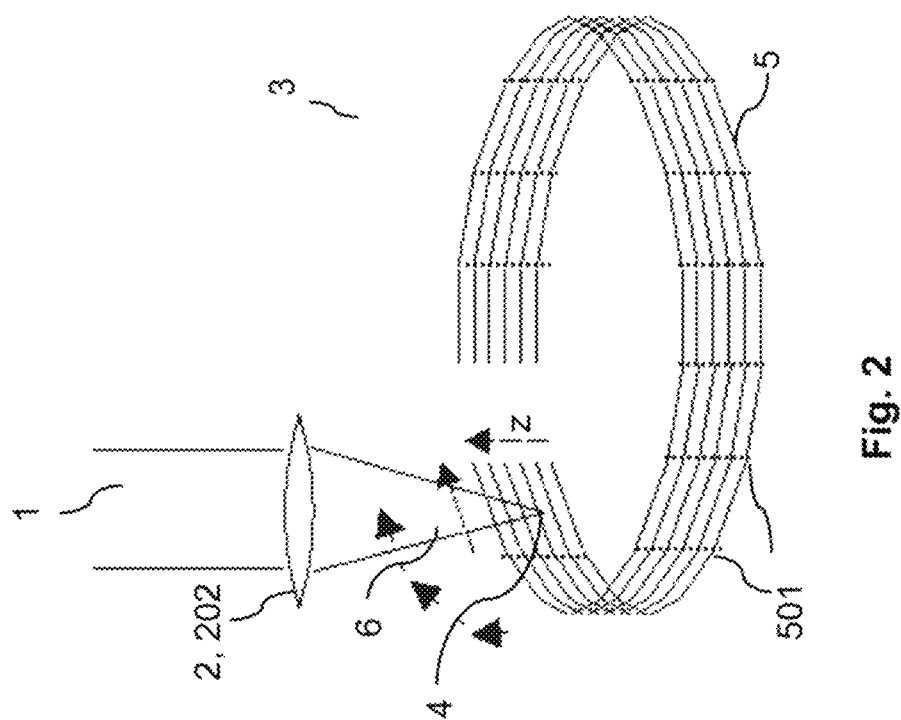

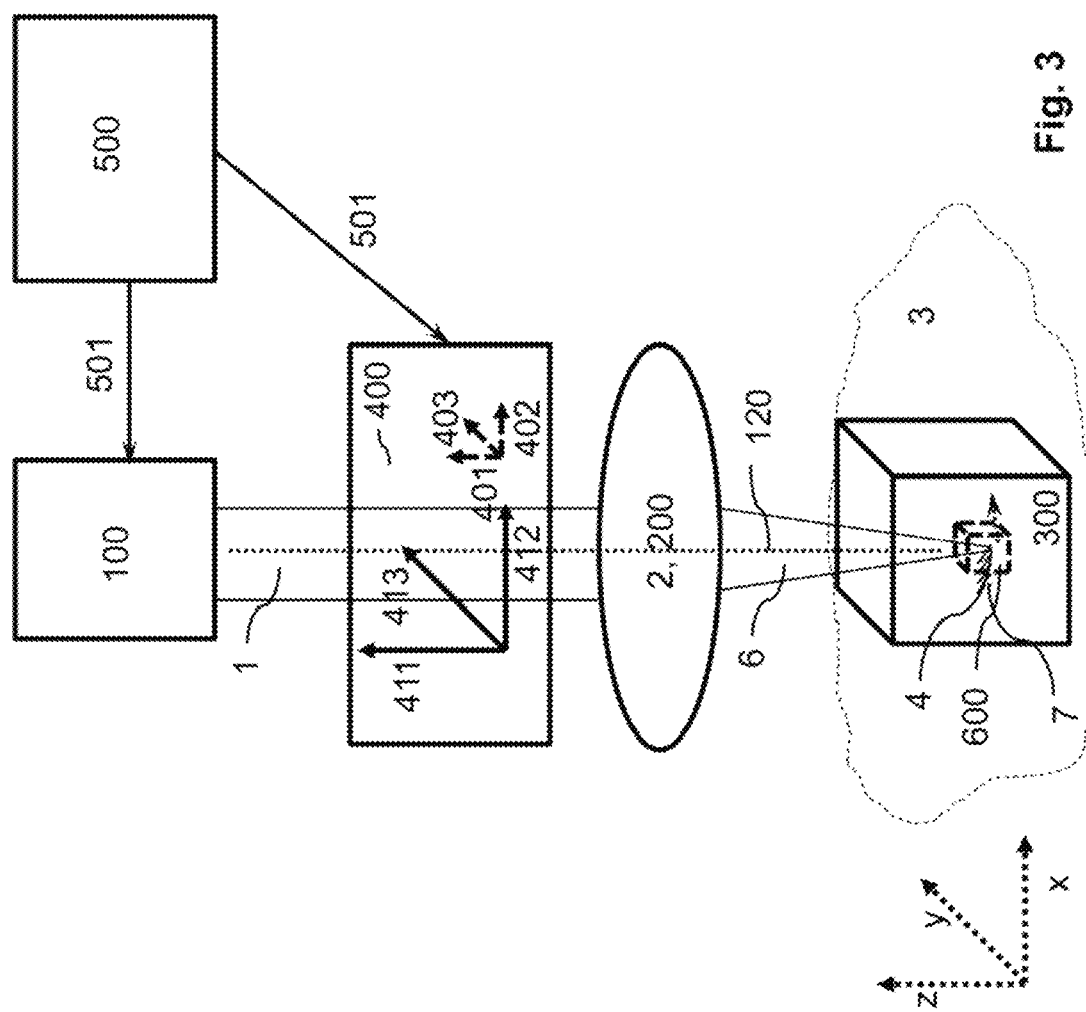

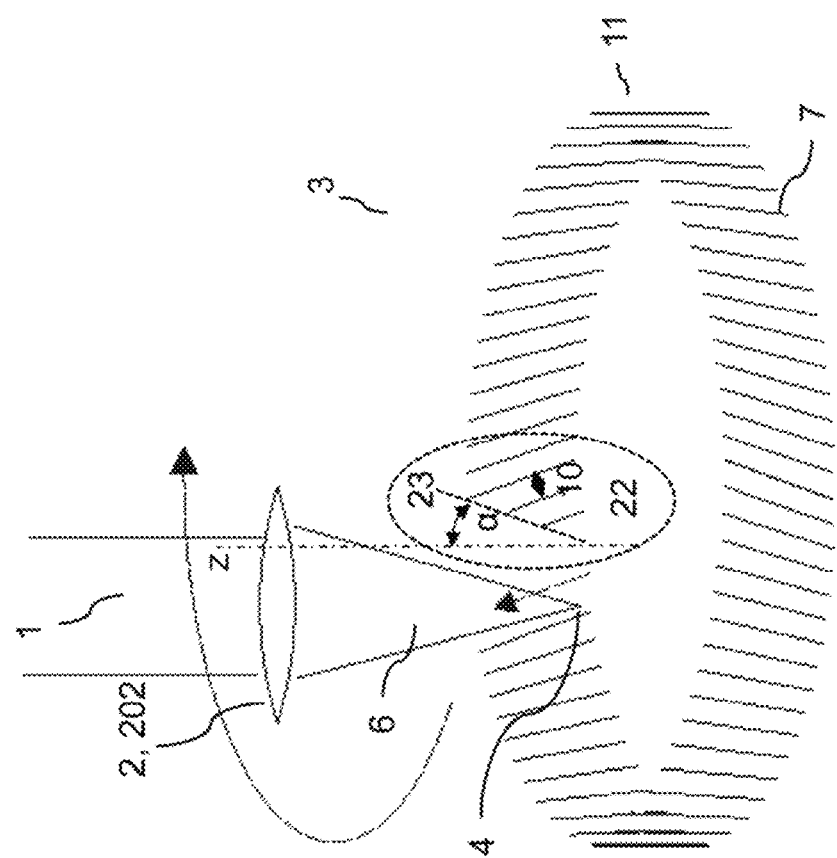

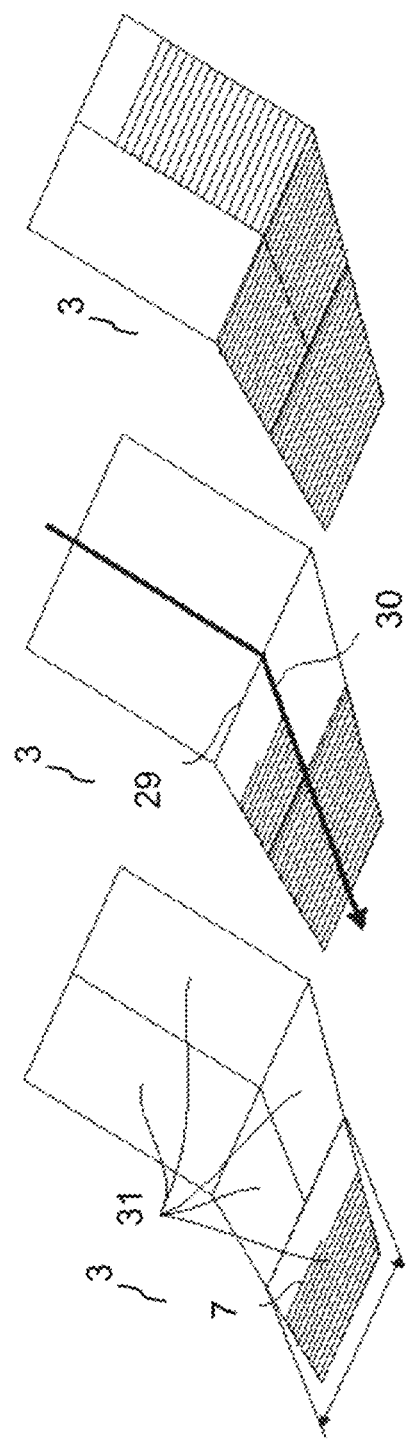

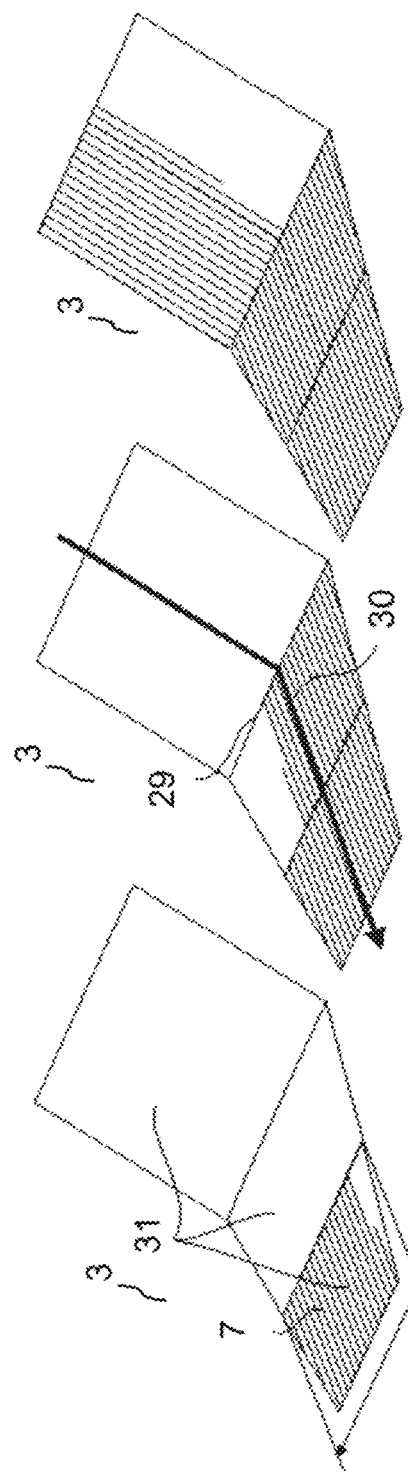

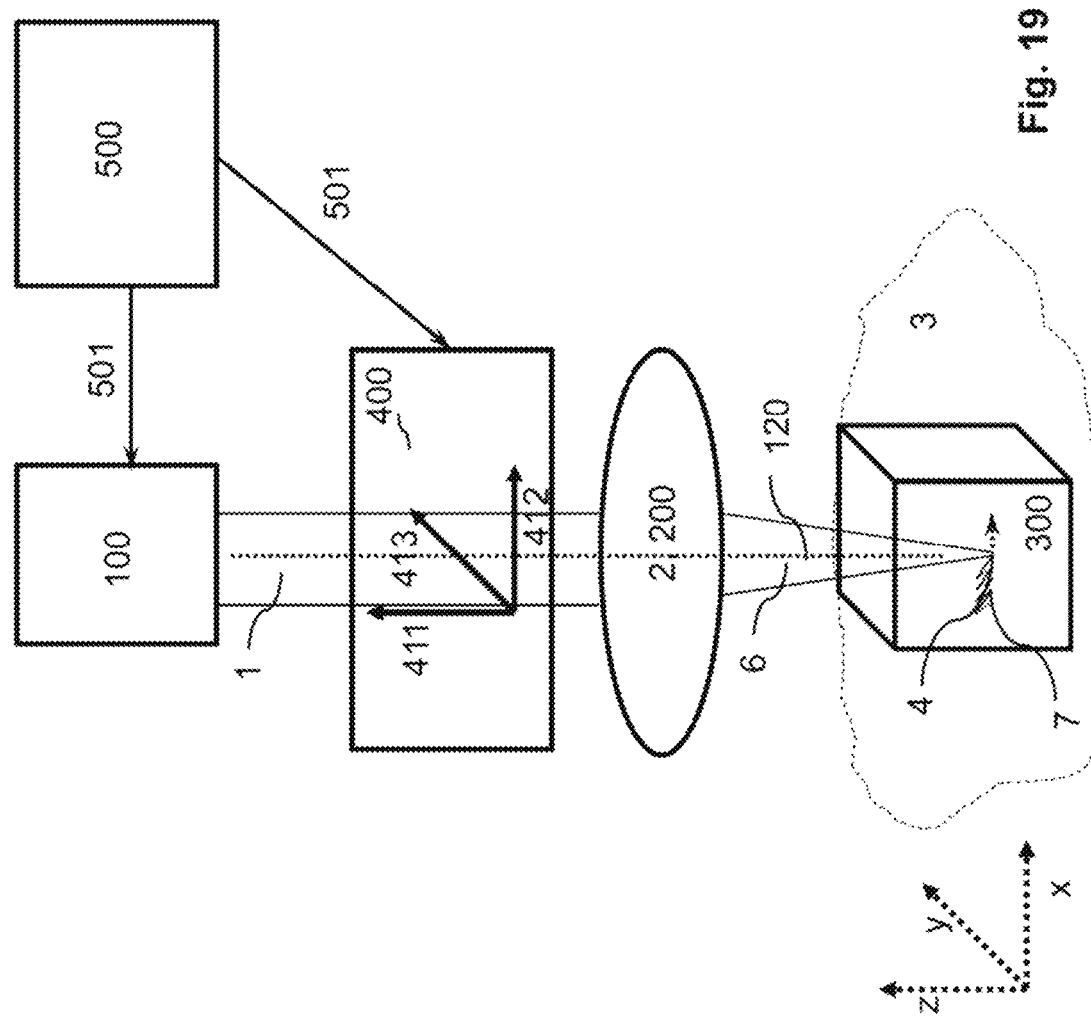

OPTHALMOLOGICAL THERAPY SYSTEM AND METHOD FOR PROCESSING A PORTION OF A PROCESSING VOLUME OF A TRANSPARENT MATERIAL BY APPLICATION OF FOCUSED RADIATION

RELATED APPLICATIONS

This application is a National Phase entry of PCT Application No. PCT/EP2016/066033 filed Jul. 6, 2016 which application claims the benefit of priority to German Application No. 102015212877.6, filed Jul. 9, 2015, the entire disclosures of which are incorporated herein by reference.

BACKGROUND

The present invention relates to a system for processing an area in a processing volume of a transparent material by application of a focused radiation, which contains a device for generating radiation, an optical system for focusing the radiation into a focus in the processing volume, a device for changing the position of the focus in the processing volume and a control device arranged to control the system. The present invention further relates to a corresponding method for processing an area in a processing volume of a transparent material by application of a focused radiation and a control program product and a planning unit for a system or a method for processing an area in a processing volume of a transparent material by application of focused radiation.

Such a device can be used in ophthalmology as an ophthalmologic therapy device, corresponding methods can be used as ophthalmologic therapy methods. The transparent material to be processed can thereby be a natural eye tissue, for example the lens, the cornea or the capsular sac, or even an artificial eye material, such as an artificial lens.

To date, so-called spiral scans are customary. These are described for example in the documents U.S. Pat. No. 5,984,916 and DE 102011085047 A1, an exemplary embodiment is shown in FIG. 1. A laser beam 1 is focused by an optical system 2, 201 in a transparent material 3. The focus 4 is thereby moved by a scanning system along a scan line 5, which is spirally here due to a lateral arbitrary closed movement such as a rotational movement, and a slow z-movement of the scanning system, through a transparent eye tissue 3. The optical system 2, 201 thereby determines the shape of the focal cone 6. In order to be able to use such a spiral scan for processing the eye tissue 3, the lateral area reachable by the optical system 2, 201 must be large enough to reach all processing areas without slow lateral movement of the optical system 2, 201. The optical system 2, 201 is correspondingly large and expensive. Due to the necessary size, this method is also only conditionally suitable for use in flexible, mobile devices with an articulated arm.

Incisions with a femtosecond laser are also known which are implemented in the vertical direction by fast scanning movements. This is called vertical z-wobble and is described for example in document WO 2013/057318 A1. FIG. 1b shows a schematic exemplary embodiment of the z-wobble. A laser beam 1 is also focused here in a transparent material 3 by use of an optical system 2, 202. The focus 4 is thereby moved through a scanning system along a scan line 5, which is generated here by a periodically recurring, fast scanning movement in the z-direction which is superposed with a slow scanning movement in an x-y plane, through a transparent eye tissue 3. Such movement for processing eye tissues 3 by use of a laser scans allows a smaller optical system 2, 202, as the fast movements are respectively carried out in a small volume. However, in unfavorable incision or processing patterns, the already generated vertical incision lines or processing lines already partially overshadow the laser focus 4 for incision lines to be applied closely adjacent thereto.

The aim is therefore to describe an apparatus and a method for processing an area in a processing volume of a transparent material, allowing it to work with a cost-efficient, thus small optical system and minimizing shadowing effects of the previously carried out incision lines or patterns in the laser focus for yet to be producing incision lines or patterns.

A possibility is provided by the lateral wobbling as disclosed in the documents EP 2412341 B1 or EP 2596773 B1 in an x-y plane.

Starting with such fast, for example oscillating lateral movements, a generation of a plane which proceeds parallel to the z-axis, is now possible by adding a small z-movement, as shown in FIG. 2. A laser beam 1 or another radiation is again focused by an optical system 2, 202 in a transparent material 3. The focus 4 is thereby moved by a scanning system along a scanning line 5, which is produced here by a periodically recurring, fast lateral scanning movement which is superimposed with a slow scanning movement in a z-direction, through a transparent eye tissue 3. Here, for example, a cylindrical incision with significant local z-extension, i.e. an extension in the z-direction which is larger than the effective area of a laser focus and thus requires several scans with the focus 4 arranged above one another, and having a lateral extension which is larger than the (partial) field, that can simultaneously be achieved with the optical system 2, 202 without additional lateral movement, can be assembled of several "patches", thus partial processing areas, in order to be able to utilize the speed advantage of the lateral wobbling. Such a procedure of "patching" is necessary when using the lateral wobbling in ophthalmology for a number of treatment patterns, particularly of incision images such as the cylindrical incision of the capsulotomy.

A lateral wobbling is possible with a system which allows a fast scanning in a plane of a processing volume perpendicular to a beam axis plane.

The assembly from several partial processing areas, however, produces many border regions 501, in which two adjacent partial processing areas have to be aligned to each other, such that, on the one hand, no "processing gap" results, and, on the other hand, regions, for which this is not intended, are not processed twice. It also leads to situations in the peripheral areas of the partial processing areas where a shadowing effect by already produced incision or processing lines becomes unavoidable.

SUMMARY OF THE INVENTION

It is thus the object of the present invention to describe a system and a method, especially for ophthalmology, for processing an area in a processing volume of a transparent material by application of a focused radiation, which permits working with a cost-efficient, thus small optical system, with which, however, the processing of the area is carried out with highest quality. In particular, shadowing effects of the processing lines or patterns already generated, also referred to as scan line or scan pattern herein, for processing lines or patterns still to be generated shall be avoided or at least minimized, boundary regions that are difficult to align to each other between two partial processing areas shall be minimized and area forms with a greatest possible flexibility shall be generated. The risk of damages to the processed transparent material shall also be minimized.

This object is solved by a system and a method for processing an area in a processing volume of a transparent material, in particular an eye by a control program product and by a planning unit.

A system is designed for processing an area in a processing volume of a transparent material, in particular of an eye, by application of focused radiation. The system may thus in particular be an ophthalmologic therapeutic system, which is used in ophthalmology for example for ophthalmologic surgical purposes, or for irradiation. However, the system is not restricted to ophthalmology according to its characteristics and functional principles, as can be seen from the explanations.

The processing area can be a two-dimensional area in a three-dimensional processing volume. However, the area may also comprise an additional curvature, thereby forming an area, which is a three-dimensional structure. In particular, the area may be a closed area in a three-dimensional processing volume.

A special case of an area to be processed is the formation of an "area" for generating a processing line in such a manner that this "area" is significantly extended in at least one spatial direction and has a minimum extension in at least one other spatial direction. Such an "area" serves for example for the opening of thin structures, in ophthalmology the implementation of a capsulotomy shall be mentioned as an example.

The processing area may be a separation area or an incision area. However, it may also be an area, on which the transparent material is removed or changed in its material properties, for example adhered.

A transparent material is a material that has only a small, virtually negligible, linear absorption in the wavelength range of the radiation used, so that an additional measure, for example, the focusing of the radiation, is required in order to generate an effect in this material.

The transparent material to be processed may be an eye tissue, as for example the cornea, the lens, the lens sac or the vitreous body. However, it may also be an artificial material, in particular an artificial eye material, such as an intraocular lens (IOL) at which are to be made corrections. The material to be processed can be of organic or inorganic nature.

The system comprises a device for generating radiation. This may be an appropriate light source or another radiation source that emits a focusable radiation. The device for generating a radiation may in particular comprise a laser, thus a device for light amplification by stimulated emission of radiation. Such a laser produces light of high intensity, usually from a narrow frequency range, with a high spatial coherence.

The use of a pulsed laser is advantageous, in particular a short pulse laser such as a femtosecond laser (fs laser) for generating a femtosecond laser beam or a picosecond laser. A pulsed laser emits light in time-limited portions, thus not continuously. It provides a high energy density.

Such a femtosecond laser or picosecond laser, for example, can hereby have a wavelength in the wavelength range from 200 nm to 2000 nm wavelength: water or eye tissue have a low linear absorption in this area and are thus a transparent material for the radiation of a femtosecond laser or picosecond laser.

Femtosecond lasers commonly in use today, which are to be used here, have a wavelength in the range of 750 nm to 1100 nm. The use of femtosecond lasers, which have a wavelength in the range of 375 nm to 550 nm or in the range of 250 nm to 367 nm, which corresponds to a doubling or tripling of the frequency of the usual femtosecond laser is also conceivable. In particular, a femtosecond laser from the wavelength range of 1020 nm to 1060 nm is used here by way of example.

The pulse duration of a femtosecond or picosecond laser, which is used here, can advantageously be chosen from a pulse duration range from 50 fs to 5 ps. In particular, a pulse duration from a range from 100 fs to 1 ps, and particularly from a range from 300 fs to 700 fs is preferred here.

The pulse energy of a femtosecond or picosecond laser used here is advantageously in a pulse energy range from 20 nJ-20 µJ.

The laser pulse repetition rate, thus the repetition rate of the laser pulses is usually chosen from a range from 10 kHz to 10 MHz, a laser pulse repetition rate from a range from 100 kHz to 1 MHz is advantageous.

The system further comprises an optical system for focusing, i.e. for bundling the radiation in a focus in the processing volume. The focal cone of such a focused radiation has a focal angle. It characterizes the aperture angle of the focus, that is, an angle of divergence, which can in principle also be expressed by the numerical aperture. The focal angle describes the angle between a line extending on the cone area of the focal cone and the optical axis. The focal angle defined in this manner thereby corresponds to half the cone angle of the focus cone. For example, the focal angle is kept approximately constant during the laser processing, also at various depths in the transparent material to be processed, as the focal length and thus the required laser pulse energy for the desired effect depends on the focal angle.

The optical system for focusing the coherent radiation in a focus allows a field of view in the processing volume with a field of view size caused by the optical system.

In the first instance, it is advantageous to be able to work with a large field of view, as the complete target field and thus the entire processing volume can then be achieved without the displacement of the optical system. An enlargement of the optical system however leads to increasing production costs of this optical system and would thus significantly increase the price of a system for processing an area in a processing volume of a transparent material.

A cost-efficient system for processing an area in a processing volume thus has a field of view size which is less than the maximum extension of an x-y-plane of the processing volume. The maximum extension of an x-y-plane of the processing volume is achieved only by the movement of the optical system, and thus by the movement of the field of view.

The focused radiation has a beam axis. It is the symmetry axis of the focused radiation and its focus cone.

The system further comprises a device for changing the position of the focus in the processing volume, which can be described by three spatial directions x, y and z. Here, the x-direction and the y-direction as lateral directions extend non-parallel to each other and respectively perpendicular to a base position beam axis, and the z-direction extends parallel to the base position beam axis, wherein the base position beam axis denotes the beam axis of the focused radiation without a deflection of the focus through the device for changing the position of the focus in the processing volume in the two lateral directions x and y.

Changing the position of the focus preferably is carried out continuously, but not necessarily with a constant speed.

A processing volume described by the circular coordinates R and φ and the direction z extending parallel to the base position beam axis direction or a processing volume described by spherical coordinates is thereby a processing volume that can be described by three spatial directions x, y and z, too: All three-dimensional coordinate systems can always be converted to one another.

The processing of an area in the processing volume is achieved by changing the position of the focal point of the focused radiation within the processing volume. At the location of the focal point of the focused radiation, an effective zone of this focused radiation occurs in the transparent material, which is referred to as focus effective zone: At the focal point and in a next surrounding around the focal point, the focused radiation changes the material transparent for a corresponding unfocused radiation.

For example, when using pulsed laser radiation and a constant speed of changing the focal position, thus the scanning speed, focus effective zones in an even distance which is determined by the pulse rate result. In a variable scan speed and a constant pulse rate of the pulsed laser radiation, the distance of the focus effective zones varies.

As a rule, a processing area comprises a plurality of focus effective zones distributed over the entire area, which maximally have such a distance from each other that the intended effect by the influence of the focused radiation is not interrupted. This leads to the corresponding processing result along the area to be processed, like an "incision" by separating the transparent material, for example by photo disruption, to a removal of material by ablation, or a change of the material, for example a bonding by coagulation of the material in the focus effective zones of a pulsed laser radiation.

The system provides the possibility to process a transparent material within the processing volume. Thus, the processing volume represents the spatial area within which the system can carry out the processing of the material based on its possibilities for spatial change of the focal point of the focused radiation, which thus represents a mobile operating point. The transparent material to be processed or the part of the transparent material to be processed is thereby ideally completely situated in the processing volume.

The system also comprises a control device which is adapted to control the system, in particular for controlling the device for generating a radiation, the device for changing the position of the focus of the focused radiation and/or the optical system. For that reason, it is connected to the device for generating a radiation, the device for changing the position of the focus of the focused radiation and/or the optical system via corresponding communication paths.

The control device can be designed in one part or in multiple parts. In a one-piece design it comprises a controller, from which all parts of the system are controlled or operated. If it is designed in several parts, it may comprise several controlling or operating devices, which are connected to each other.

The control device can be encoded with a control program product, or to be encoded with a control program product that is either on a data carrier, wherein the data carrier is brought in connection with the control device for the purpose of encoding, or the control program product is provided via the internet or via any other external storage space for download, wherein the control device can connect to the internet or to another external storage space in a direct manner or via intermediate steps.

A planning unit as a delimiting partial unit can thereby be comprised in the control device, which is designed to implement all steps of the planning or provision of a therapy guidance, in particular of parameters of the beam generation, the focus as well as of scan movements for processing an area, in a chronological sequence. The planning unit is designed to plan and/or to provide a scan pattern as temporal change of the position of a focus of the radiation and thereby of focus effective zones in the material to be processed.

With a control device in several parts, such a planning device can also represent a unit which is independent from other units of the control device, and which is connected to the other units of the control device via communication paths.

In one embodiment, the planning unit may comprise a selection table of scan patterns. In another configuration, it comprises an algorithm for creating a scan pattern.

If a control device containing such a planning unit is encoded, the scan movements, in particular the scan pattern, are provided by this planning unit.

According to the invention, the device for changing the position of the focus of the system is designed to perform, in an arbitrary direction determined by the three spatial directions, a slow scanning movement in the processing volume of the transparent material and—also in an arbitrary direction determined by the three spatial directions—a fast scanning movement independent of the slow scanning movement in a section of the processing volume. The section of the fast scanning movement can thereby be moved by the slow scanning movement in the entire processing volume. Thus, a complete fast three-dimensional scanning system cooperates with a slow independent three-dimensional scanning system in such a manner, that the fast three-dimensional scanning system respectively accesses a partial section or a partial volume of the entire processing volume. This partial section can however be moved through the entire processing volume with the help of the slow three-dimensional scanning system.

The possible size of the section of the fast scanning movement is determined by the field of view of the optical system that is used, but also by the type of the generation of the fast scanning movement.

The terms "slow" and "fast" are defined here relative to one another and are used to identify the two base scanning movements and scanning systems. The fast scanning movement is carried out with a maximum speed, which is a multiple of the maximum speed of the slow scanning movement. For example, the fast scanning movement may be ten times to a thousand times of the slow scanning movement. A fast scanning movement that is about one hundred times of the slow scanning movement is advantageous in another example.

Typical sizes of the processing volume in which a slow scanning movement is carried out, can, for a processing device, which is used for example as an ophthalmologic therapy device, be in any spatial direction between 2 mm and 25 mm, for example, between 5 mm and 12 mm. This volume can typically be scanned with speeds in a range from 1 to 100 mm/s, for example, of about 10 mm/s.

A typical size of a section simultaneously accessible by the fast scanning movement is between 0.5 mm and 2 mm in any spatial direction. For example, a three-dimensional section of about 1 mm×1 mm×1 mm can be achieved by the fast scanning movement. Scanning movements of several hundred Hertz are possible thereby.

The arbitrary, changeable direction determined by the three spatial directions results for the fast and for the slow scanning movement by vector addition of the respective scanning parts in the three spatial directions x, y and z per time unit for the fast scanning movement and for the slow scanning movement. By vector addition of the direction of the fast and the direction of the slow scanning movement for the same time unit, a total direction of the two scanning movement's then results for this time unit.

The system according to the invention thereby permits on the one hand to scan a section of the processing volume at a high speed and to scan the total processing volume at a significantly slower speed: A focus of the focused radiation movable through the processing volume with a slow scanning movement in an arbitrary and changeable direction during the course of a scanning process corresponding to a desired pattern is therefore subject to an additional fast scanning movement in a second arbitrary, changeable direction which is superposed with the slow scanning movement during the course of the scanning process. This additional fast scanning movement is, however, always only allowed in a small section of the processing volume.

The high speed at which the fast scanning movement is carried out, additionally allows, when using a pulsed laser from the picosecond or femtosecond range, which has a high laser pulse repetition rate, to distribute the focus effective zones correspondingly in the processing volume and to position them not too close to each other.

This "division of labor" between slow and fast scanning movement permits to use scanning systems for the fast scanning movement, which are capable to change the position of the focus extremely rapidly, as they do not have to move any large, heavy optical system, while the optical system can be moved with the slow scanning movement with other scanning systems.

A system, for example an ophthalmologic therapy system, comprises a control device, in which a scan pattern is encoded, which has a sequence of focus effective zones of the focused radiation along a scan line. The sequence of focus effective zones is thereby encoded in an advantageous embodiment of the system according to the invention such that focus effective zones that have already been realized are always arranged outside a focal cone for focus effective zones still to be realized, the focal cone being described by the focus of the focused radiation and the focal angle.

Herein, the scan line is the line or the track that results or would result, when the focus of the focused radiation, and thus also the focal cone, is moved by application of the device for changing the position of the focus in the processing volume, and it is or would be a continuous radiation. The scan line can be a straight line, or else be curved either completely or partially in a plane or in a three-dimensional space.

The scan line thus describes the location of the focus in the processing volume reached during the scanning process in dependence on the time, regardless if the focused radiation just comes into effect or does not come into effect. The actual focus effective zones of the focused radiation are then set along the scan line.

Thus, when scanning, the focal cone is guided on a scan line through the processing volume in such a manner that the focal cone never intersects the part of the scan line already covered, then the condition that focus effective zones that have already been realized are always arranged outside of a focal cone for focus effective zones yet to be realized, is fulfilled in any case. But the condition can also still be fulfilled, if, during scanning, positions result, in which a possibly imaginary focal cone intersects the part of the scan line already covered: This is the case if no focus effective zones were realized in the cut area or in the cut areas of the scan line, or if a cut region indeed contains realized focus effective zones, but the focused radiation remains shadowed as long as its imaginary focal cone is in the region of focus effective zones which have already been realized.

This condition is fulfilled in a simple manner when a scan pattern is designed such that the focus effective zones, which are located in the beam path of the radiation furthest from the device for generating the radiation, are first applied: The other focus effective zones are then realized successively in the direction of larger z-values, thus towards the radiation source. Thus, if a scan pattern shall result in a region that is smaller than the section in which the fast scanning movement can be carried out, the scan pattern may be encoded and realized in this manner. This is also a solution if a next scan pattern or a next part of a complex scan pattern shall be created with a distance from said first scan pattern of the first section, wherein the focal cone of the focused radiation for the focus effective zones of the scan pattern to be realized in the second section does not comprise already realized focus effective zones of the scan pattern of the first section, which would be the case, if the second scan pattern or the second part of a complex scan pattern shall not be set directly subsequent to the first pattern.

If, however, both sections shall be placed next to each other, especially over a wide z-region, perhaps because the processing area shall be continued seamlessly, then some focus effective zones already realized will be arranged at least in a boundary region in the focal cone of focus effective zones yet to be realized. If these are also to be avoided, these boundary regions first have to be omitted in dependence on the size of the focal angle of the focal cone of the focused radiation and be filled successively at the end.

The system for example, contains a device for changing the position of the focus, which comprises a fast z-scanner for fast scanning in a direction parallel to the base position beam axis and at least one fast lateral scanner for fast scanning in a plane vertical to the base position beam axis for realizing the fast scanning movement in the section of the processing volume in addition to a slow z-scanner for slow scanning in a direction parallel to the base position beam axis and at least one slow lateral scanner for slow scanning in a plane vertical to the base position beam axis for realizing the slow scanning movement in the processing volume.

By cooperation of one or several fast lateral scanners and the fast z-scanner controlled in dependence on a desired direction of the fast scanning movement, a fast scanning movement is possible in an arbitrary, changeable direction in a section of the processing volume.

For the slow scanning movement in the processing volume, a slow z-scanner which is independent of the fast z-scanner and one or more slow lateral scanners, which are also independent of the respective fast lateral scanners are provided, whose cooperation is also controlled in accordance with of the desired direction.

In one embodiment of the system, the faster lateral scanner is formed by a fast x-scanner, which is present in addition to a further fast lateral scanner. This further fast lateral scanner is formed by a fast y-scanner. The fast x-scanner and the y-fast scanner can thereby also be present in a common x-y-scanning unit. Such an x-y-scanning unit that actually contains a fast x-scanner and a fast y-scanner can for example be realized by a gimbal scanner.

In an alternative embodiment, a fast lateral scanner is formed by a fast R-scanner whose scanning movement can be aligned in an x-y-plane vertical to the base position beam axis by rotation about a rotation axis parallel to the base position beam axis about an angle $\Phi$. The rotation itself can be carried out slowly.

Some alternative embodiments are in principle also possible for the slow lateral scanner or scanners.

The slow and the fast lateral scanning can therefore consist of the movements of an x- and a y-scanner, wherein the movements of the x-scanner and the y-scanner are matched to one another such that a desired direction of the scanning movement results in the x-y-plane. Alternatively, the lateral scanning can be carried out in a desired direction of the scanning movement in the x-y plane by a R scanner, wherein the direction of the scanning movement is controlled in that the R-scanner is aligned by a rotation by an angle Φ about a rotation axis parallel to the base position beam axis.

In a particular embodiment, the system contains a fast z-scanner, which comprises a lens element oscillating in the z-direction. This oscillating lens element is for example a negative lens, thus a concave lens, which acts, together with a fixed positive lens, thus a convex lens, as a beam widening telescope. In principle, a positive lens, thus a convex lens, can also be selected as the oscillating lens element. But then, the position of an intermediate focus must be paid attention to.

In this embodiment, the system further contains a fast two-dimensional lateral scanner, which comprises an x-y-mirror element movable about two axes or two individual mirror elements respectively movable about one axis, whose axes are for example perpendicular to each other. By application of this fast lateral scanner, a fast movement in the lateral plane is possible, thus the x-y-plane, in particular a fast oscillating movement in the x-y-plane.

In this embodiment, the system also contains a slow z-scanner, which comprises a lens element optionally movable in the z-direction, again for example a negative lens, which acts together with a fixed positive lens as beam expansion telescope, and a slow lateral scanner, which comprises a focusing optical system optionally displaceable in the lateral plane. The optical system for focusing can thus be displaced laterally, wherein the directed radiation is directed on this focusing optical system by mirrors moving along in a fixed relation to the displaceable focusing optical system.

In one example embodiment of the system, synchronous changes of direction of the fast scanning movement are carried out in at least two spatial directions. This is implemented by the synchronous change of direction of at least two fast scanners. The synchronous changes of direction of at least two fast scanners are carried out in a defined temporal relationship to each. For example, they can be carried out simultaneously. Alternatively, however, a defined temporal offset of the synchronous changes of direction of at least two faster scanners is possible.

The fast scanners thus pass along predetermined space-time curves, which are synchronized with each other. It is not necessarily required that these are synchronized to the movement of the slow scanners.

The synchronous changes of direction of the fast scanning movement in at least two spatial directions can thereby be carried out periodically and can be carried out by synchronous periodic changes of direction of at least two fast scanners. The fast scanners in the corresponding spatial directions thus change their direction temporally coordinated to each other in a defined period.

In particular, this can be carried out in a simple manner by synchronous oscillatory movements of at least two fast scanners.

A synchronous oscillatory movement of two fast lateral scanners, thus a fast x-scanner and a fast y-scanner, enables the processing of an area perpendicular to the base position beam axis. If this exceeds the achievable section of the processing volume, which can simultaneously be achieved by the fast scanners, a superposition of a slow scanning movement in the x- and/or y-direction is necessary, in order to process such an area. If oscillatory movements of two fast lateral scanners that are synchronized to each other, are superimposed with a slow scanning movement, which also contains a z-component, then processing areas as shown in FIG. 2 are possible.

One of these fast scanners can for example be a resonant scanner, the other fast scanners must then be able to be synchronized on its resonant frequency. That is, that one of at least two fast scanners is then a resonant scanner with a free oscillation, and all others of the at least two fast scanners are synchronized to the resonant scanner. This synchronization is advantageously phase-locked.

By using a resonant scanner, it is possible to significantly increase the scanning frequency, and thus the scanning speed in comparison to a pure use of non-resonant scanners, a factor of 5 to 10 is possible hereby.

Another example is an embodiment in which the fast scanning movement is carried out by synchronous oscillatory movements of the fast z-scanner and at least one fast lateral scanner, thus a fast x- and/or y-scanner, or the R-scanner.

For example, altogether six-scanners are used in the system according to the invention. For each spatial direction x, y and z respectively there is a fast scanner which carries out oscillating movements. This permits to scan a three-dimensional section of the processing volume of about 1 mm×1 mm×1 mm with several hundred Hertz. In addition there is a slow scanner for each spatial direction x, y and z, which permits to achieve the complete necessary processing volume.

For processing of an area in a processing volume, the movement for realizing a scan pattern along the scan line is assembled from a slow scanning movement and a fast scanning movement by the fast scanners synchronously oscillating with each other in a system according to the invention, which can perform a fast scanning movement independently of a slow scanning movement in every arbitrary direction in the processing volume, and which, for realizing the fast scanning movement of the synchronous oscillatory movements uses at least two fast scanners, and in particular, the synchronous oscillatory movements of a fast z-scanner and at least one, usually two fast lateral scanners in the form of an x-scanner and a y-scanner.

The slow scanning movement can thereby be performed at a constant speed or at a varying speed in dependence on the location and/or time. It has a lateral component in the x-direction and/or in the y-direction.

It is the aim to create a scan pattern such that a focus effective zone which is already realized is always arranged outside the focal cone of a focus effective zone still to be realized. It is therefore important that an oscillating, thus "swinging" scanning movement is performed such that minimum z-values are reached when it swings ahead in a slow "feeding direction". Thus, focus effective zones still to be realized are always placed above focus effective zones which are already realized.

The oscillatory movement of the fast z-scanner is therefore synchronized to the oscillatory movement of a fast lateral scanner or two fast lateral scanners in the form of a fast x- and/or fast y-scanner fast so that, at a positive lateral component of the slow scanning movement in the x- and/or y-direction, the oscillatory movements of the fast lateral scanner, in particular of the fast x-scanner and/or the fast y-scanner, are in phase opposition to the oscillatory movement of the fast z-scanner and that with a negative lateral component of the slow scanning movement in the x- and/or y-direction, the oscillatory movements of the fast lateral scanner, in particular of the fast x-scanner and/or the fast y-scanner, are in phase to the oscillatory movement of the fast z-scanner The oscillatory movement of the fast z-scanner between a minimum z-value and maximum z-value is therefore synchronized to the movement of a fast oscillatory lateral scanner or two fast lateral scanners in the form of a fast x- and/or a fast y-scanner, which oscillate between a minimum x-value and a maximum x-value and/or a y-minimum value and a maximum y-value.

The amplitude of the oscillatory movement can thereby change temporally or spatially. The maximum and minimum x-, y- and z-values of the oscillatory movement in a section of the processing volume are therefore not to be regarded as a constant.

Thereby, at least two oscillatory movements are synchronized to each other such that—the maximum x-value of the fast lateral scanner occurs in the x-direction, thus of the fast x-scanner, and/or the maximum y-value of the fast lateral scanner occurs in the y-direction, thus of the fast y-scanner, with a minimum z-value of the fast z-scanner and the minimum x-value of the fast lateral scanner occurs in the x-direction and/or the minimum y-value of the fast lateral scanner occurs in the y-direction at a maximum z-value of the fast z-scanner for a lateral component of the slow scanning movement in the positive x- and/or y-direction, and—the minimum x-value of the fast lateral scanner occurs in the x-direction and/or the minimum y-value of the fast lateral scanner occurs in the y-direction at a minimum z-value of the fast z-scanner and the maximum x-value of the fast lateral scanner occurs in the x-direction, and the maximum y-value of the fast lateral scanner occurs in the y-direction at a maximum z-value of the fast z-scanner for a lateral component of the slow scanning movement in the negative x- and/or y-direction.

Once there is a lateral component of the slow scanning movement is present in the same direction, in which an oscillatory movement of a fast lateral scanner for the realization of the fast scanning movement, and additionally an oscillatory movement of a fast z-scanner is present, one has to pay attention to the mentioned conditions during the synchronization of the fast scanners with each other: This enables the realization of a scan pattern such that focus effective zones result on inclined scan lines and focus effective zones already realized are always arranged outside a focal cone for focus effective zones still to be realized, the focal cone being formed by the focus of the focused radiation and the focal angle.

The slow scanning movement can thereby also have a component in the z-direction. Regarding a slow scanning movement in the z-direction, the synchronization of two fast movements with a periodic change of direction, in particular the phase position of the synchronization of the oscillatory movement of a fast z-scanner with at least one fast lateral scanner is however not of importance. However, the slow scanning movement in the z-direction always has to be carried out in the positive direction, thus parallel to the base position beam axis and against the beam direction of the radiation.

Furthermore, in an example embodiment a system comprising a control device is advantageous, into which a scan pattern is encoded, which comprises adjacent strokes. A stroke comprises an essentially straight part of a scan line, and is realized by a juxtaposition of focus effective zones of the focused radiation on this part of the scan line.

A stroke thereby does not necessarily describe a straight line: Curvatures or deviations from a straight line of several degrees to several ten degrees are possible. The part of the scan line comprised by a stroke is rather aligned in a direction in the processing volume of the system, so that it does not comprise any reversing points of the fast scanning movement in the x-, y- and/or z-direction. When the scan line passes a reversing point of the fast scanning movement, a next stroke results thereafter.

Adjacent strokes have an essentially same distance. The fact that the distance does not have to remain exactly the same means that the distance of adjacent strokes can fluctuate by several percent, whereby a maximum distance should not be exceeded, so that the intended effect by the influence of the focused radiation is not interrupted. Already by a changing curvature or alignment of a stroke compared to the adjacent stroke, an exactly the same distance of the adjacent strokes over their entire length is often not possible.

The strokes respectively have angles of inclination, wherein the angle of inclination of a stroke is the angle between the stroke and the beam axis. The angles of inclination of two adjacent strokes are not necessarily the same, the inclination angle can also change along a stroke. For a curved stroke, the decisive angle of inclination is the smallest angle between a tangent to the curvature line of the stroke and the beam axis.

However, the scan pattern must be encoded in this embodiment of the system according to the invention in such a manner that the respective angle of inclination of the stroke to the beam axis is larger or equal to the focal angle of the focused radiation.

The condition that the inclination angle of the stroke to the optic axis must be larger than the focal angle of the focused radiation, thereby applies for each individual stroke and at any point of the stroke—the latter condition is important for curved strokes. The condition is fulfilled by the consideration of the smallest angle, as shown above.

Regardless of their angle of inclination, for strokes superposed in the direction of the beam axis and against the beam direction of the radiation or crossing strokes, a following stroke is always realized over the adjacent preceding stroke, so that the condition that focus effective zones already realized are always arranged outside of a focal cone for focus effective zones still to be realized, is fulfilled.

If the strokes are generated by the superposition of a slow and a fast scanning movement, wherein the fast scanning movement is realized by synchronous oscillatory movements of a fast z-scanner and at least a fast lateral scanner, then the mentioned conditions regarding minimum and maximum values for the synchronization have to be noted; the necessary angle of inclination can be generated by a corresponding ratio of slow and fast scanning movement.

In a variant of a system according to the invention, the control device is thus encoded such that the formation of a stroke is always realized by stringing together focus effective zones of focused radiation only in an upward movement along the scan line or only in a downward movement along the scan line: An upward movement is thereby a movement with a z-component against the beam direction, while a downward movement is a movement with a z-component in the direction of the beam direction.

If the strokes are generated by a synchronous oscillatory movement of a fast z-scanner and at least one fast lateral scanner, focus effective zones are always set only in a half period of the oscillatory movement. When the slow scanning movement superimposed over the fast scanning movement is constant, this results in regularly arranged strokes. When the lateral component of the slow scanning movement is identical to the direction of the oscillatory movement of the at least one lateral scanner, the strokes always have the same distance to each other.

By using the downward movement, it is advantageous if the angle of inclination of the strokes to the beam axis is larger than the focal angle of the focused radiation, so that a focus effective zone already realized is also not arranged on the cone area of the focal cone of a focus effective zone still to be realized.

In another variant of a system according to the invention, the control device is encoded so that the formation of the strokes is realized alternately through stringing together focus effective zones of focused radiation in a upward movement and a downward movement along the scan line. Thereby strokes result with essentially two different angles of inclination, but advantageously focus effective zones can be realized here during the entire period of the oscillatory movement.

In one embodiment of the system according to the invention, the device for generating radiation comprises a pulsed laser with a laser pulse repetition rate. A distance of a focus effective zone of a preceding focus effective zone is then given by the laser pulse repetition rate and an overall scanning speed, which is composed of the scanning speeds of slow and fast scanning movements.

The scanning speeds are thereby not necessarily constant. In particular for the oscillatory movement, the speed is the highest at a zero transition of the oscillation, and the lowest at the reversal point, thus at the minimum value and at the maximum value of the oscillatory movement.

It is then of particular advantage if the control device is adapted to mask a laser pulse, when its focus effective zone falls below a minimum distance to the preceding focus effective zone. Damages in the transparent material to be processed can thereby be avoided, which can occur when several focus effective zones are realized at the same position or at positions close to each other in the processing volume.

In this example embodiment of the system according to the invention, several advantageous characteristics are thus combined, which mutually influence each other positively in order to process a processing area precisely and with a high quality with a focused radiation, without causing damage.

By stringing strokes together, which have an angle of inclination to the optical axis, which is larger than the focal angle on the one hand, thus large enough that existing focus effective zones from the part of the scan pattern already realized are penetrated by the focused radiation only in areas behind the focal point of the focused radiation, there is no shadowing. When the strokes on the other hand have an angle of inclination which is smaller than 90°, area shapes can be generated thereby which have no border regions, or for the special case of closed areas, at maximum have a border region to already completed focus effective zones. By masking laser pulses in dependence on the speed of the overall scanning movement composed of the fast and slow scanning movement damage in the transparent material to be processed, especially damage in an ocular tissue, is avoided. In addition, a processing of an area with such a scan pattern leads to an efficient filling of the processing area. In case of an incision area generated by the focus effective zones of a pulsed laser, for example a femtosecond laser, this leads to a clean cut area, in which the risk of tears is minimized.

A system according to the invention thus allows the effective, time-saving arrangement of focus effective zones, in particular of laser focus effective zones, in a scan pattern which takes into account characteristics of the device for change of the position of the focus, in particular of a scanning system comprised herein, to only have quickly accessible a section of the three-dimensional processing volume, but to be able to move this section slowly through the entire processing volume. The latter allows the use of an cheap focusing optical system with a small field and the restricted width of a fast focus depth adjustment.

If, due to only a small extent of the processed area, a small, cost-efficient optical system is sufficient, without the latter having to be then moved, or if the achieved speed of processing is not relevant even in extensive areas to be treated, then the system for processing an area in a processing volume of a transparent material by application of a focused radiation, in particular an ophthalmologic therapy device, comprising a device for generating a radiation and an optical system for focusing the radiation into a focus in the processing volume, wherein the focus of the focused radiation has a focal angle and the focused radiation has a beam axis according to the above given definitions. The device for producing a focusable radiation may comprise a laser, preferably a pulsed laser and in particular a short pulse laser such as a picosecond or femtosecond laser having the characteristics described above.

The system further includes a device for changing the position of the focus of the focused radiation by a scanning movement in an arbitrarily changeable processing volume, wherein the processing volume and thus the scanning movement and a scan pattern resulting from it is determined by three spatial directions x, y and z. Herein, the x-direction and the y-direction are non-parallel to each other and respectively normal to a base position beam axis and the z-direction is parallel to the base position-beam axis, which denotes the beam axis of the focused radiation without deflection of the focus through the device for changing the position of the focus in the processing volume in the two lateral directions x and y. Changing the position of the focus is for example carried out continuously, but not necessarily at a constant speed. For this purpose, the device for changing the position of the focus may comprise three mutually independent scanners, for example an x-scanner, y-scanner and a z-scanner. These scanners may also be characterized as to the achievable processing volume and speeds by the values mentioned above. Also, the slow x-scanner can be combined with the slow y-scanner in an x-y scanning unit.

The system is characterized by a control device which is adapted to control the system, in particular for controlling the device for generating a radiation, the device for changing the position of the focus of the focused radiation and/or the optical system. For that purpose it is connected to the device for generating a radiation, the device for changing the position of the focus of the focused radiation and/or the optical system via appropriate communication paths The control device may again be designed in one piece or in several parts. According to an example embodiment of the invention, a scan pattern is encoded into the control device, which can be realized by the scanning movement along a scan line, said scanning movement comprising at least one lateral base component in the x- and/or y-direction. The scanning movement can also further comprise a base component in the z-direction.

However, the scanning movement is not characterized by an constant movement in an arbitrary direction: rather, a lateral base component in the x- and/or y-direction and optionally also a base component in the z-direction is superimposed by components of synchronous change-of-direction-movements in the z-direction and in at least one of the lateral spatial directions x- and/or y. The synchronous change-of-direction-movements are therefore portions of an overall movement in a corresponding direction, which are composed of the respective base component and the respective change-of-direction-movements in this direction.

The synchronous change-of-direction-movements in the z-direction and in at least one of the lateral spatial directions x- and/or y can thereby be carried out in a defined temporal relationship to each other. In particular, the changes of direction can occur simultaneously. Alternatively, however, a defined temporal offset of the synchronous changes of direction is possible.

The synchronous change-of-direction-movements in the z-direction and in at least one of the lateral directions in space x- and/or y can be effected periodically.

The lateral base component in the x- and/or y-direction is superimposed by the synchronous change-of-direction-movements in the z-direction and in x-direction and/or in the y-direction, which are synchronized with each other such that, for a positive lateral base component of the scanning movement in x- and/or y-direction, the change-of-direction-movements in the x- and/or y-direction are in phase opposition to the change-of-direction-movements in the z-direction, and that at a negative lateral base component of the scanning movement in the x- and/or y-direction, the periodic change-of-direction-movements in the x- and/or y-direction are in phase to the periodic change-of-direction-movements in the z-direction.

A lateral base component invariantly directed in the x- and/or y-direction and optionally also a base component invariantly directed in the z-direction is thus superimposed to the change-of-direction-movements in the z-direction between a minimum z-reversal point and a maximum z-reversal point, which are synchronized to change-of-direction-movements in at least one lateral spatial direction x- and/or y between a minimum x-reversal point and a maximum x-reversal point and/or between a minimum y-reversal point and a maximum y-reversal point. The value of the respective x-, y- or z-reversal point is generally not a constant but may be varied within the possibilities of the processing volume.

In this case, at least two change-of-direction-movements are synchronized to each other such that the maximum x-reversal point and/or the maximum y-reversal point correspond to a minimum z-reversal point and the minimum x-reversal point and/or the minimum y-reversal point correspond to a maximum z-reversal point for a lateral base component in the positive x- and/or y-direction and the minimum x-reversal point and/or the minimum y-reversal point correspond to a minimum z-reversal point and the maximum x-reversal point and/or the maximum y-reversal correspond to a maximum z-reversal point for a lateral base component in the negative x- and/or y-direction.

However, the resulting scanning movement is not the result of the interaction of several scanning movements which are generated by different scanning systems or with different scanners, but it is realized by one scanning system, for example using one scanner for each of the spatial directions x, y and z, which are part of the device for changing the position of the focus in the processing volume.

When there is a lateral base component invariantly directed in the same direction, in which the change-of-direction-movements are carried out, and additionally change-of-direction-movements are carried out in the z-direction, the mentioned conditions have to be considered when synchronizing the change-of-direction-movements among each other: This allows to realize a scan pattern such that focus effective zones on inclined scan lines result, during whose generation as few as possible shadowing effects are effective by structures of the already processed regions of the processing area.

Such a proceeding, which is locally very limited at every moment is for example favorable in eye surgery in order to minimize the impact of a possible movement of the eye during the surgery. In contrast to the prior art, with the system according to the invention—as well as a corresponding process—the entire processing volume is not processed over a long period, and always only a small part of an incision plane is completed, which otherwise would lead to an offset within an incision plane during movements of the eye, the incision plane then being possibly not completely carried out. With the system according to the invention and the corresponding method on the other hand, the incision is immediately completed locally.

By a corresponding selection of the invariantly directed lateral base component in the x- and/or y-direction and the speed and the "amplitude" of the change-of-direction-movements in the respective lateral spatial direction x- and/or y and their implementation by encoding into the control device, a scan pattern is encoded in an example system according to the invention, which has a sequence of focus effective zones of the focused radiation along a scan line, such that focus effective zones already realized are always arranged outside of a focal cone, which is formed by the focus of the focused radiation and the focal angle, for focus effective zones still to be realized, as the inclination of the scan lines to the beam axis can be determined hereby.

Another example is a system in whose control device a scan pattern is encoded which has mutually adjacent strokes with inclination angles to the beam axis, wherein a stroke comprises a straight section of the scan line and is realized through stringing together focus effective zones of focused radiation, and wherein the angles of inclination of the strokes are larger or equal to the focal angle of the focused radiation. With such a scan pattern, a sequence of the arrangement of the focus effective zones is accomplished such that focus effective zones already realized are always arranged outside a focal cone which is formed by the focus of the focused radiation and the focal angle for focus effective zone which are still to be realized.

For an arrangement of strokes with an inclination angle to the beam axis a subsequent stroke is thus realized above the adjacent stroke, whereby "above" means an arrangement in a direction opposite to the beam direction.

The control device can be encoded such that the formation of the strokes by stringing together focus effective zones of focused radiation is always in an upward movement, or always in a downward movement or realized alternately in an upward movement and a downward movement along the scan line.

The device for generating a radiation of a system according to an example embodiment of the invention may comprise a pulsed laser with a laser pulse repetition rate, wherein a distance of a focal effective zone from a preceding focus effective zone is determined by the laser pulse repetition rate and a scanning speed. Then it is advantageous if the control device is set up to mask a laser pulse, when its focus effective zone falls below a minimum distance to the preceding focus effective zone.

Processing an area in very high quality also requires reducing or ideally avoiding completely damages to the processed transparent material. A system for processing an area in a processing volume of a transparent material by application of a focused radiation, in particular an ophthalmologic therapy system, comprises a device for generating a radiation that comprises a pulsed laser with a laser pulse repetition rate, and an optical system for focusing the radiation into a focus in the processing volume, a device for changing the position of the focus of the radiation focused in the processing volume, and a control device adapted to control the system.

Again, the device for generating a radiation can comprise a pulsed laser, in particular a short pulse laser such as a picosecond or femtosecond laser having the characteristics described above. The device for changing the position of the focus can include a scanning system with an x-scanner, a y-scanner and a z-scanner. These can be characterized with respect to the achievable processing volume and speeds by the above mentioned values.

In such a device, a distance of a focal effective zone from a preceding focus effective zone is determined by the laser pulse repetition rate and a scanning speed that can vary spatially and temporally. The control device of the system according to the invention is arranged to avoid damages of the transparent material to be processed, by masking a laser pulse, if a distance of the focus effective zone of the laser pulse to the preceding focus effective zone is below a minimum distance.

This is particularly the case with oscillating scanning movements, in which there are respectively reversal points at which the speed of the corresponding scanning movement in the direction in question approaches zero. It is useful, for example, with oscillations in the z-direction, to mask the laser pulses in a region around the upper and the lower reversal point, thereby avoiding closely spaced focus effective zones, or even more to avoid focus effective zones on identical locations.

A method for processing an area in a processing volume of a transparent material, in particular an eye, by a focused radiation by application of a system, which comprises a device for generating a radiation and an optical system for focusing the radiation into a focus in the processing volume, which can be described with three spatial directions, x, y and z, is characterized in that the position of the focus of the thus focused radiation is changed by a slow scanning movement in the processing volume of the transparent material and a fast scanning movement in a section of the processing volume in any, by the three spatial directions determined direction. The section of the fast scanning movement is, however, moved by the slow scanning movement in the entire processing volume. The z-direction is parallel to the base setting beam axis.

Both the slow and the fast scanning movement is thus possible in an arbitrary direction in the processing volume. The fast scanning movement is carried out with a maximum speed, which is a multiple of the maximum speed of the slow scanning movement.

Here, the focus has a focal angle, which characterizes the opening angle of the focus and describes the angle between a straight line extending in the cone surface of the focal cone and a beam axis of the focused radiation.

Preferably in a method according to the invention, a scan pattern is realized in the transparent material by generating a sequence of focus effective zones of the focused radiation along a scan line in such a way that already realized focus effective zones are always arranged outside a focal cone, which is formed by the focus of the focused radiation and the focal angle, for focus effective zones still to be realized It is advantageous according to example embodiments, if in a method according to the invention for processing an area in a processing volume of a transparent material synchronous changes of direction of the fast scanning movement are carried out in at least two directions in space: This allows processing of a section of the processing volume quickly and effectively, while this section can be moved through the entire processing volume by application of the slow scanning movement.

The synchronous changes of direction thereby are carried out in a defined temporal relationship to each other. In particular, they can be carried out simultaneously. Alternatively, however, a defined temporal offset of the synchronous changes of direction of the fast scanning movement in at least two directions in space is possible.

The synchronous changes of direction of the fast scanning movement in at least two spatial directions can also be carried out periodically.

For example, such a fast scanning movement is carried out by synchronous oscillatory movements in at least two directions in space. By using a fast oscillating scanner for each of the spatial directions x, y and z the oscillatory movements of the fast z-scanner are therefore synchronized with those of fast x-scanner and/or the fast y-scanner.

If a fast z-scanner is used in conjunction with a fast R-scanner, which can be rotated about the optical axis, the fast z-scanner is synchronized with the fast R-scanner.

Hereby one of these fast scanners can be a resonant scanner, the other fast scanners must then be able to be synchronized on that resonant frequency.

In particular, according to example embodiments, it is advantageous for the method according to the invention when the fast scanning movement is carried out by synchronous oscillatory movements in the z-direction and in at least one of both lateral spatial directions x and y.

It is particularly advantageous, for example, if a method, in which a slow scanning movement is carried out with a lateral component in the x-direction and/or in y-direction, and the fast oscillatory movements in the z-direction and in x-direction and/or y-direction are synchronized to each other such that, for a positive lateral component of the slow scanning movement in the x- and/or y-direction, the fast oscillatory movements in the x-direction and/or y-direction occur in phase opposition to the oscillatory movement in the z-direction, and that, for a negative lateral component of the slow scanning movement in x- and/or y-direction, the fast oscillatory movements in the x-direction and/or y-direction occur in phase with the oscillatory movement in the z-direction.

In such a method according to an example embodiment of the invention, therefore, the fast oscillatory movement between a minimum z-value and maximum z-value for the fast oscillatory movement between a minimum x-value and a maximum x-value and/or a minimum y-value and a maximum y-value are synchronized such that
 the maximum x-value and/or the maximum y-value is achieved at a minimum z-value and the minimum value of x- and/or the minimum y-value is achieved at a maximum z-value for a lateral component of the slow scanning movement in positive x- and/or y-direction, and
 the minimum x-value and/or the minimum y-value is achieved at a minimum z-value and the maximum x-value and the maximum y-value is achieved at a maximum z-value for a lateral component of the slow scanning movement in negative x- and/or y-direction.

The amplitude of the oscillatory movement can thereby change temporally or spatially.

In an advantageous embodiment of the method according to an example embodiment of the invention, a scan pattern is generated, which has mutually adjacent strokes with inclination angles to the beam axis, wherein a stroke comprising a straight section of a scan line and is implemented by a series of focus effective zones of focused radiation, wherein the inclination angle of the strokes to the beam axis is larger or equal to the focal angle of the focused radiation.

The inclination angle of the stroke to the beam axis can vary in this case, but it may never be less than the focal angle of the focused radiation.

The latter condition must always apply, that is, for each stroke at any point of the stroke, to guarantee that realized focus effective zones of adjacent strokes already realized are not located in the focal cone of a focus effective zone still to be realized. In compliance with this condition, a stroke to be realized thereby respectively is carried out above the adjacent stroke already realized, thus in compared to the previous stroke, in the positive z-direction.

The strokes may be formed in an alternative embodiment of the method according to the invention in that focus effective zones of the focused radiation are always lined up in an upward movement, or always in a downward movement along the scan line. In another alternative, the strokes can alternately be aligned in an upward movement and a downward movement along the scan line.

The scanning movements are not necessarily carried out at a constant speed. In particular for oscillatory movements, the speed of the scanning movement is the highest at the zero transition of the oscillation, and lowest at the reversal point, that is the maximum value or minimum value of the oscillatory movement. Also the slow scanning movement can be carried out as a movement with an adjustable speed.

In an advantageous embodiment of the method according to the invention, the device for generating a radiation generates a pulsed laser radiation with a laser pulse repetition rate. The distance of a focal effective zone from a preceding focus effective zone is determined by the laser pulse repetition rate and an overall scanning speed, which is composed of the scanning speeds of the slow and fast scanning movements.

If a distance of a focus effective zone now falls below a specified minimum distance to the preceding focus effective zone, the laser pulse is masked and the focus effective zone is not realized. This minimum distance is determined such that a repeated input of energy by two or more successive laser pulses at the focal point in a processed transparent material in close proximity to the preceding energy input, or even in the same place, is avoided, and it therefore does not result in unwanted changes of the material. Damages in the material will therefore be avoided.

Procedurally, the embodiments of the invention allow for areas to be processed having a low expansion or without any demands on the speed of processing by a method for processing a surface in a processing volume of a transparent material, in particular an eye, by a focused radiation by application of a system comprising a device for generating radiation and an optical system for focusing the radiation into a focus in the processing volume, which is determined by three spatial directions x, y and z, wherein the position of the focus of the thus focused radiation is changeable by a scanning movement in the processing volume of the transparent material in any arbitrary direction, determined by the three spatial directions x, y and z, and wherein a scan pattern is generated in the transparent material along a scan line by the action of the focused radiation during the scanning movement. Therein, the z-direction is arranged parallel to a base position beam axis.

According to the invention, a scanning movement is carried out thereby having at least a lateral base component in the x- and/or y-direction. The scanning movement can further also comprise a base component in the z-direction. For determining this scanning movement, the lateral base component is superimposed in the x- and/or y-direction and possibly also the base component in the z-direction is superimposed by components of synchronous changes of direction movements in the z-direction and in at least one lateral spatial direction x- and/or y, wherein the change-of-direction-movements are synchronized to each other such that, with a positive lateral base component of the scanning movement in the x- and/or y-direction, the change-of-direction-movements are carried out in the x- and/or y-direction opposite to the change-of-direction-movements in the z-direction, and that, with a negative lateral base component of the scanning movement in the x- and/or y-direction, the change-of-direction-movements in the x- and/or y-direction are carried out in the same direction as the change-of-direction-movements in the z-direction.

The synchronous change-of-direction-movements thereby are carried out in the z-direction and in at least one of the lateral spatial directions x- and/or y in a defined temporal relation to each other. In particular, the changes of direction movements can occur simultaneously. Alternatively, however, a defined temporal offset of the synchronous changes of direction is possible.

The synchronous change-of-direction-movements in the z-direction and in at least one of the lateral spatial directions x- and/or y can also be carried out periodically.

An invariably directed lateral base component in the x- and/or y-direction and optionally also an invariably directed base component in the z-direction is thus superimposed to the change-of-direction-movements in the z-direction between a minimum z-reversal point and a maximum z-reversal point, which are synchronized to the change-of-direction-movements in at least one lateral spatial direction x- and/or y between a minimum x-reversal point and a maximum x-reversal point, and/or between a minimum y-reversal point and a maximum y-reversal point.

These changes of direction movements being carried out in at least two spatial directions are synchronized to each other such that the maximum x-reversal point and/or the maximum y-reversal point is achieved at a minimum z-reversal point and the minimum x-reversal point and/or the minimum y-reversal point is achieved at a maximum z-reversal point for a lateral base component in positive x- and/or y-direction and the minimum x-reversal point and/or the minimum y-reversal point is achieved at a minimum z-reversal point and the maximum x-reversal point and/or the maximum y reversal point is achieved at a maximum z-reversal point for a lateral base component in negative x- and/or y-direction.

The scanning movement is realized by a scanning system, for example using a scanner for each of the spatial directions x, y and z.

In an advantageous example embodiment of the method according to the invention, a scan pattern is generated by a series of focus effective zones of the radiation focused along a scan line in the transparent material. This scan line is thereby controlled such that focus effective zones already realized are always arranged outside a focal cone for focus effective zones still to be realized. The focal cone is determined by the focus of the focused radiation and the focal angle, which describes the angle between a straight line extending along the cone surface and focus the beam axis.

In an advantageous example embodiment of the method according to the invention, a scan pattern is generated, which has mutually adjacent strokes with inclination angles to the beam axis, wherein a stroke comprises a straight part of a scan line and is realized by stringing together focus effective zones of focused radiation, and wherein the inclined angle of the strokes to the beam axis is larger or equal to the focal angle of the focused radiation.

A stroke can be formed in that focus effective zones of the focused radiation are always lined up in an upward movement, or always in a downward movement along the scan line. Alternatively, a stroke can be formed in that focus effective zones of the focused radiation are alternately lined up in an upward movement and downward movement along the scan line.

Another method according to the invention for processing an area in a processing volume of a transparent material by a focused radiation is effected by application of a system which comprises a device for generating a radiation, in which a pulsed laser radiation is generated with a laser pulse repetition rate, and an optical system for focusing the radiation at a focal point in the processing volume, wherein the position of the focus of the focused radiation is changed by a scanning movement in the processing volume of the transparent material. A distance of a focal effective zone from a preceding focus effective zone is determined in this process by the laser pulse repetition rate and a scan speed, and a laser pulse is then masked when the distance of the focus effective zone from the preceding focus effective zone falls below a minimum distance.

Embodiments of the invention furthermore include a control program product, i.e., a computer program product that can be used to control a system.

The control program product according to the invention is configured for encoding a control device of a system for processing of an area in a processing volume of a transparent material by application of a focused radiation.

In particular, in one example embodiment variant, such a control program product provides an encoding of a scan pattern in such a manner that it is composed by fast scanning movements in a section of the processing volume and slow scanning movements in the processing volume in an arbitrary direction determined by three spatial directions, wherein the section of the fast scanning movement can be moved by the slow scanning movement in the entire processing volume.

For realizing the fast scanning movement, a scan pattern can be encoded in an example embodiment of the control program product according to the invention such that synchronous change-of-direction-movements of the fast scanning movement are carried out in at least two spatial directions, in particular, that a fast scanning movement is generated by synchronous oscillatory movements of at least two fast scanners, wherein synchronous oscillatory movements of the fast z-scanner and at least one fast lateral scanner being advantageous.

A control program product for encoding a fast scanning movement by the synchronized oscillatory movements of the fast z-scanner between a minimum z-value and a maximum z-value and a fast lateral scanner or two fast lateral scanners in the form of a fast x- and/or fast y-scanner, which oscillate between a minimum x-value and a maximum x-value and/or a minimum y-value and a maximum y-value, is for example advantageous. The at least two oscillatory movements are synchronized with one another such that the maximum x-value of the fast x-scanner, and/or the maximum y-value of the fast y-scanner is achieved with a minimum z-value of the fast z-scanner, and the minimum x-value of the fast x-scanner and/or the minimum y-value of the fast y-scanner is achieved with a minimum z-value of the fast z-scanner for a lateral component of the slow scanning movement in the positive x- and/or y-direction; and the minimum x-value of the fast x-scanner, and/or the minimum y-value of the fast y-scanner is achieved with a minimum z-value of the fast z-Scanner, and the maximum x-value of the fast x-scanner and/or the maximum y-value of the fast y-scanner is achieved with a maximum z-value of the fast z-scanner for a lateral component of the slow scanning movement in the negative x- and/or y-direction.

For realizing the scanning movement, in a more general, example embodiment of control program product according to the invention, a scan pattern can be encoded such that a scanning movement with a lateral base component in the x-direction and/or in the y-direction, if necessary also with an additional base component in the z-direction, which determines a base movement, which for example provides a invariably directed movement, is superimposed with synchronous change-of-direction-movements in the z-direction and in the x-direction and/or y-direction, which are synchronized to each other such that, with a positive lateral base component of the scanning movement in the x- and/or y-direction, the change-of-direction-movements in the x- and/or y-direction are carried out in the opposite direction to the changes-of-direction-movements in the z-direction, and that, with a negative lateral base component of the scanning movement in the x- and/or y-direction, the change-of-direction-movements in the x- and/or y-direction are carried out in line with the change-of-direction-movements in the z-direction.

In a control program product according to the invention, a scan program product is preferably encoded in a manner that it has a sequence of focus effective zones of focused radiation along a scan line, such that focus effective zones already realized are always arranged outside a focal cone, which is formed by the focus of the focused radiation and the focal angle for a scan pattern still to be realized.

A particularly preferred control program product according to the invention comprises the encoding of a scan pattern of mutually adjacent strokes with inclination angles to a beam axis of the focused radiation, wherein a stroke includes a straight section of a scan line, and is realized by a series of focus effective zones of the focused radiation, and wherein the angle of inclination of the strokes to the beam axis is equal or larger to the focal angle of focused radiation.

A scan pattern can further be encoded by a control program product in such a manner that the formation of a stroke by stringing together focus effective zones of the focused radiation is always realized in an upward movement or is always realized in a downward movement along the scan line, or that the formation of the strokes is realized through stringing together focus effective zones of focused radiation alternately in upward movement and downward movement.

An example embodiment of the control program product according to the invention for a system which comprises a device for generating radiation in the form of a pulsed laser radiation with a laser pulse repetition rate comprises an encoding of a scan pattern such that a laser pulse is masked when the distance of its focus effective zone to the preceding focus effective zone falls below a minimum distance.

BRIEF DESCRIPTION OF THE DRAWINGS

The present invention shall now be explained by use of example embodiments. It is shown in:

FIG. 2: the realization of an incision area in a processing volume of a transparent material by lateral wobbling as described above.

FIG. 3: a first example of a system for processing an area in a processing volume of a transparent material by application of a focused radiation.

FIG. 9: the advantageous juxtaposition of inclined scan lines for processing a closed, cylindrical area.

FIGS. 17a to 17c: a first scan pattern for generating an access incision in different phases.

FIGS. 18a to 18c: a second scan pattern for generating an access incision in different phases.

FIG. 19: a second example of a system for processing an area in a processing volume of a transparent material by application of a focused radiation.

DETAILED DESCRIPTION

Figure 1B:
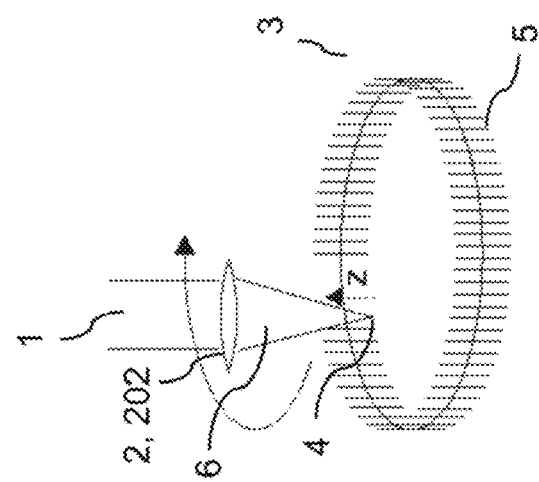
FIGS. 1a and 1b: the realization of two incision areas in a processing volume of a transparent material by application of an optical radiation according to the prior art as described above.
Figure 1A:
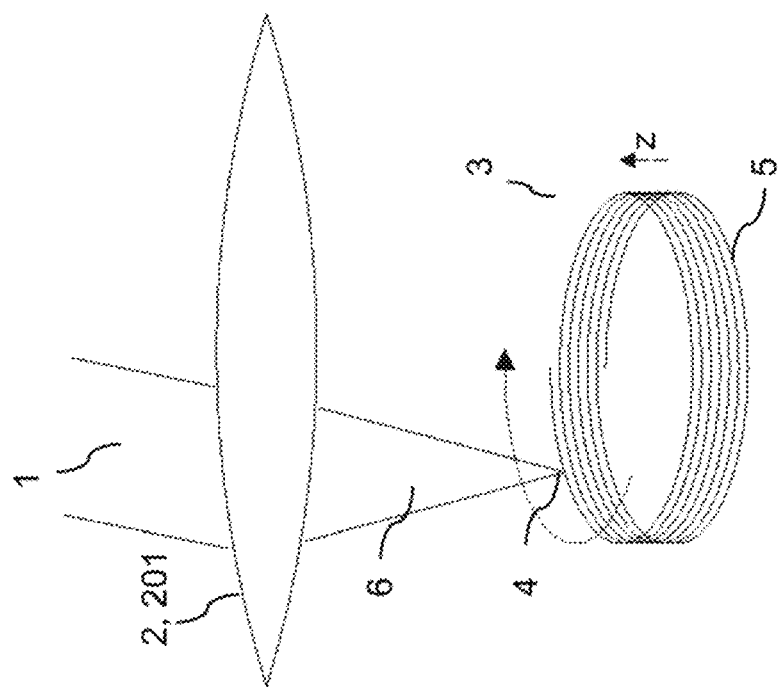

FIG. 3 shows a first example of an ophthalmologic therapy system for processing an area in a processing volume of a transparent material by application of a focused radiation.

The system comprises a device for generating a radiation 100 comprising a femtosecond laser with a wavelength in the range of 1020-1060 nm. The pulse duration of this femtosecond laser is 500-600 fs, the pulse energy about 10 µJ and the laser pulse repetition rate about 100 kHz.

In addition, the system comprises an optical system 2, 200 for focusing the radiation in a focus 4, with a numerical aperture of 0.2, which has a field of view of about 1 mm.

The system also includes a device for changing the position of the focused radiation. This device can carry out, in any arbitrary direction determined by the three spatial directions, a slow scanning movement in the processing volume 300 of the transparent material 3, here the eye, and a fast scanning movement, which is independent of the slow scanning movement, in a section 600 of the processing volume 300, wherein the section 600 of the fast scanning movement can be moved by the slow scanning movement in the entire processing volume 300.

Altogether six-scanners are used. For each of the spatial direction x, y and z, where the z-direction extends parallel to the initial base position beam axis 120 and the x- and y-direction extend vertical to the base position beam axis 120, there is respectively a fast scanner 401, 402, 403, which allows to scan a section 600 of about 1 mm×1 mm×1 mm of the three-dimensional processing volume 300 with several hundred Hertz. In addition there is a slow scanner 411, 412, 413 for each spatial direction. These allow the complete necessary processing volumes 600 of about 15 mm×15 mm×15 mm for the generation of incisions in an eye tissue 3.

The overall implemented scanning movement at a time t is composed of slowly changeable components in the x-, y- and z-direction, which are identified by the index s, and rapidly changeable components in the x-, y- and z-direction, which are identified by the index f:

$$\begin{pmatrix} x(t) \\ y(t) \\ z(t) \end{pmatrix} = \begin{pmatrix} x_s(t) \\ y_s(t) \\ z_s(t) \end{pmatrix} + \begin{pmatrix} x_f(t) \\ y_f(t) \\ z_f(t) \end{pmatrix}.$$

The slowly changeable components ($x_s$, $y_s$, $z_s$) can show an arbitrary time behavior and must only remain below a maximum speed $v_{max}$ and/or a maximum acceleration $a_{max}$.

$$\frac{dx(t)}{dt} \le v_{max}; \quad \frac{d^2 x(t)}{dt^2} \le a_{max} \text{(dito für } y(t) \text{ und } z(t)\text{)}.$$

The rapidly changeable components ($x_f$, $y_f$, $z_f$) are not subject to these restrictions. However, for the area filling, recurring similar movement paths have to be passed, and the strokes 7 are generated therewith. An example of recurring similar movement paths, which shall not be restricting at this point, would be an oscillation with a period T:

$$x_f = X(t)\sin\left(2\pi \frac{t}{T}\right) + O(t).$$

The amplitude X and a center position O may thereby slowly change with time, too, similar to the slow components of the scanning movement. It is only necessary that recurring similar movement paths, thus the traversed locus curves, are similar. That these will always pass through in similar times, is not mandatory but a typical realization. In conjunction with the slow movement, similar strokes 7 are then placed close together and form an incision area 11.

The system further comprises a one-piece central control system 500, which is connected via the communication paths 501 to the device for generating a radiation 100, thus the femtosecond laser system, and to the device for changing the position 400 of the focus 4, and which is adapted to control the femtosecond laser system and all scanners 401, 402, 403, 411, 412, 413 of the device for changing the position 400 of the focus 4.

In this example, the laser pulse repetition rate is 100 kHz. Neighboring focus effective zones shall have a distance of about 10 μm. The scanning speed of the fast scanners is about 1000 mm/s. With a size of about 1 mm×1 mm×1 mm of the section 600 of the processing volume 300 for the fast scanners 401, 402, 403, 100 pulses in 1 ms are resulting. Thereafter, the slow scanning movement should also have achieved a progression of about 10 μm in the corresponding direction. The slow scanners 411, 412, 413 thus have a scanning speed of about 10 mm/s. This will This system is used for the generation of incisions by photo disruption by application of the femtosecond laser. With this system, for example, access incisions of a lateral size of 2 mm, a capsulotomy with a lateral diameter of 5 mm or relaxation incisions in the cornea over a lateral diameter of 11 mm can be carried out. In the depth, thus in the z-direction, for simple incisions, where a certain inclined position shall be considered, an incision depth of 500 μm can be generated, a lens thickness of 3-5 mm can be penetrated, or other incisions in the cornea or the lens of 10 to 12 mm depth can be carried out.

Figure 4:
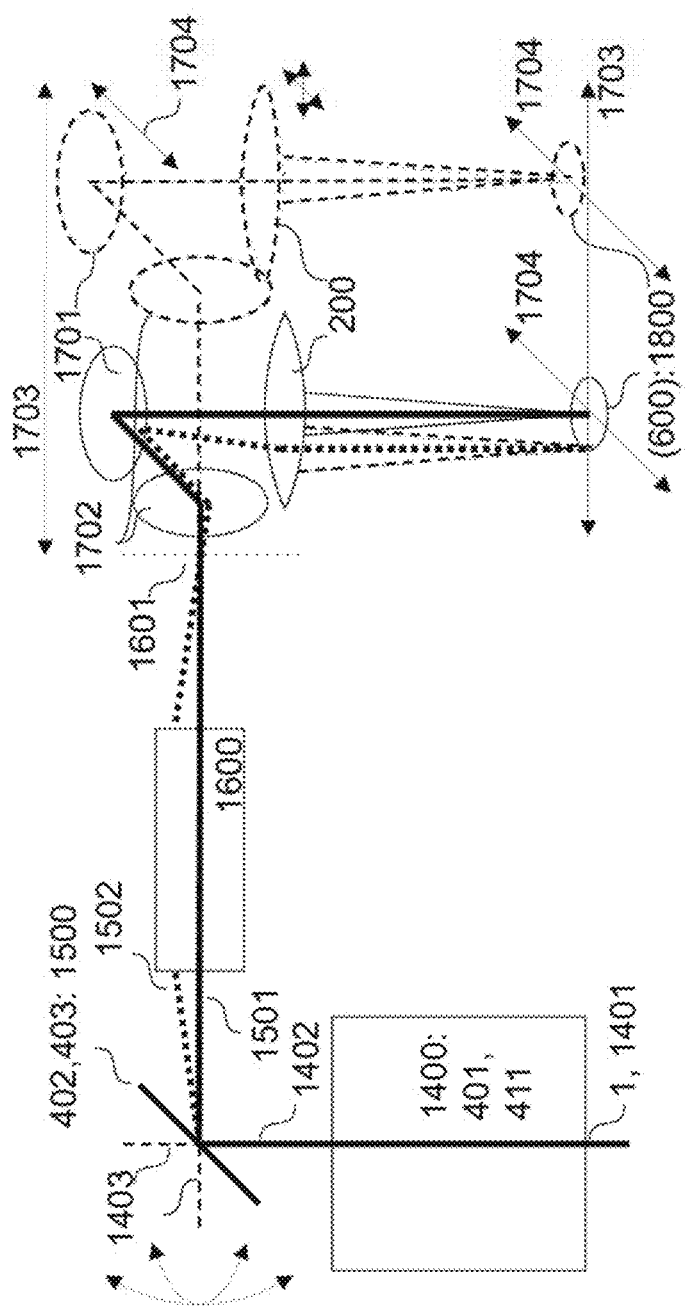
FIG. 4: a scheme of the entire optical structure of an ophthalmologic therapy system according to the invention with an optical system for focusing a radiation and a device for changing the position of the focus of the radiation.

FIG. 4 shows a scheme of the entire optical structure of an ophthalmologic therapy system with a focusing optical system 200 for focusing a radiation 1 and a device for changing the position of the focus of the radiation. This can for example be used in the first example of the ophthalmologic therapy system of FIG. 3.

A z-scan module 1400, 401, 411 generates, from the input beam 1401 with constant divergence, constant deflection and constant diameter, a beam with modulated divergence, but still constant deflection and constant diameter in the exit pupil 1403.

A fast x/y-scanner 402, 403—a so-called partial field scanner 1500—which can be swiveled about two perpendicular axes and thereby carry out oscillating movements about a zero point about both axes, additionally implies a lateral deflection upon the divergence-modulated beam 1402, which creates a deflected divergence-modulated beam 1502 from the non-deflected, divergence-modulated beam 1501.

The pupil plane 1403, in which the beam diameter is constant, is imaged from the relay 1600 into the entrance pupil 1601 of the focusing optical system 200, so that the beam at that point shows a constant diameter but a divergence- and deflection modulation. The focused beam thus has an approximately constant numerical aperture NA, which is independent of the divergence, thus the z-position of the focus 4 and the deflection, thus the x-y-position of the focus 4.

The lateral partial scan field 1800 of the fast x/y scanner, thus the x-y-extension of the section 600 of the fast scanning movement, can additionally be moved by an optional lateral displacement of the focusing optical system 200. The tracking of the beam with the movement of the focusing optical system 200 is effected by the mirrors 1701 and 1702, which respectively move along the axis of the non-deflected beam impinging thereon. The mirror 1701 moves in the direction 1704, which shall be the y-direction here, as well as in direction 1703, which shall be the x-direction, and the mirror 1702 in direction 1703, thus the x-direction, which here is arranged perpendicular to the y-direction 1704. The movement of the mirrors 1701 and 1702 is thereby coupled to the movement of the focusing optical system.

Figure 5:
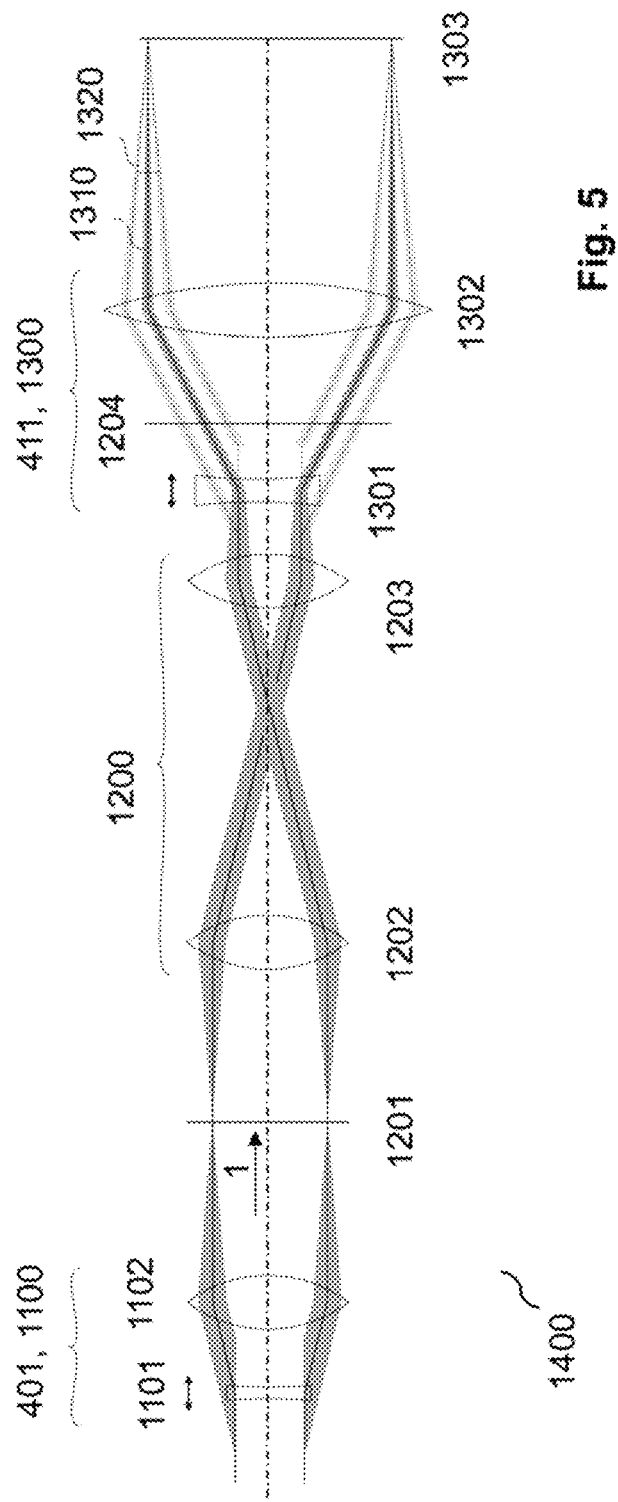
FIG. 5: a z-scan module of a fast and slow scanner.

FIG. 5 shows details of a z-scan module 1400, which comprises a fast z-scanner 401 and a slow z-scanner 411. A first beam-widening telescope is thereby configured as the fast z-scanner 401. It contains a lens 1101 movable along the z-direction, which is oscillated about its zero position in a fast manner. It is advantageous to arrange such a fast oscillating lens, as shown here, in the beam path near the radiation source 100, as the beam still has a small diameter here, and this movable lens 1101 can be designed as a smallest, lightest element at this location. A negative, thus concave lens as the movable lens 1101 of the beam-widening telescope effects an oscillation of the beam divergence with a constant beam diameter in the exit pupil 1201.

A relay telescope 1200 images the exit pupil 1201 of the fast z-scanner 401 into the entrance pupil 1204 of a further beam-widening telescope 1300. This further beam-widening telescope 1300 is designed as a slow z-scanner 411 with an optional z-t-curve and a wide scanning range in such a manner that the entire height z of the processing volume 300 (see FIG. 4) can be scanned. For this, the lens 1301 can be moved in a controlled manner with arbitrary location-time curves, but limited in speed and acceleration.

In the exit pupil 1303 of this z-scan module 1400, a beam with an optionally slowly adjustable divergence is then available in a wide adjustment range 1320 with a fixed beam diameter, whose divergence additionally oscillates with a fixed amplitude given by the amplitude of the oscillation of the lens 1101 in a smaller angle range or adjustment range 1310 about the zero position with the slow but optionally movable lens 1301.

Figure 6:
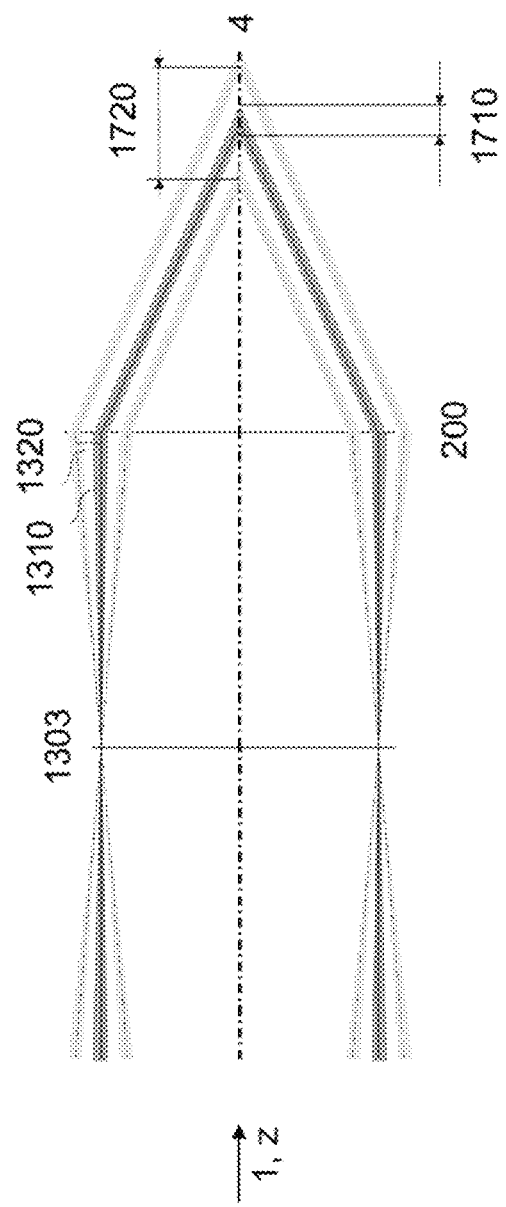
FIG. 6: the change of divergence during the movement of the focus in the z-direction.

FIG. 6 shows the divergence change with a movement of the focus 4 in the z-direction. The focusing optical system 200 transmits the fast divergence oscillation in the angle range 1310, which is caused by the fast z-scanner, and the slow divergence variation in the angle range 1320, which is caused by the slow z-scanner, into an oscillation of the z-position of the focus 4 in the z-area 1710 and variation of the zero position of the oscillation in the z-area 1720. The aperture angle of the focused beam, thus the numeric aperture NA, remains constant when the exit pupil 1303 of the slow scanner 411 is placed into the entrance pupil of the focusing optical system 200.

Figure 7:
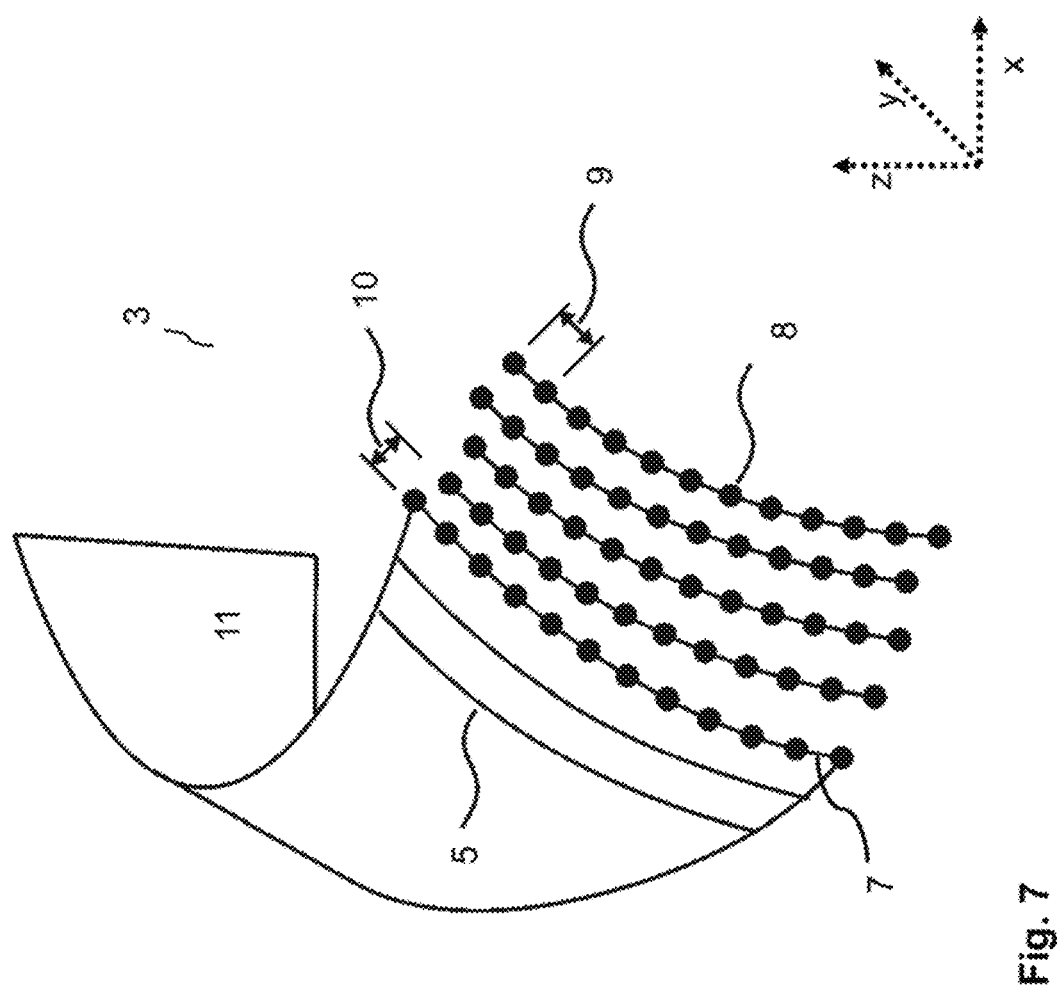
FIG. 7: the structuring of a scan pattern for an area to be processed in a processing volume.

In FIG. 7, the principal structure of a scan pattern is illustrated for an area 11 to be processed in a three-dimensional processing volume of a transparent material, concerning a multiple curved incision area 11 in this example, which is to be generated using a pulsed laser radiation.

Such a scan pattern consists of individual strokes 7 which are respectively realized by a sequence of laser focus effective zones 8 on a scan line 5. The individual strokes 7 are lined up in rows to the desired incision area 11 so that they fill the incision area 11 and that the individual laser focus effective zones 8 have an approximately same distance 9 not only to their preceding and subsequent laser focus effective zones 8 on the same stroke 7, but also to the laser focus effective zones 8 of the adjacent strokes 7, wherein fluctuations of the distance, for example, by a factor of 2, are unproblematic. Here, each stroke 7 remains within the currently accessible section of the optical system 2, 200, but may slowly displace for forming the area 11. The incision area 11 then has a "band-shaped" form.

Due to the flexibility of scanning movements, thus the possibility for movement in an arbitrary direction in the processing volume 300, and in particular when using a system which enables a fast scanning movement in an arbitrary direction in a section 600 of the processing volume 300 independently of a slow scanning movement in an arbitrary direction in the processing volume 300, an arbitrary curvature with a high quality can be achieved by an advantageous arrangement of the individual strokes 7.

The strokes 7 are realized in this example by a synchronous oscillatory movement of a fast z-scanner 401 and the fast lateral scanner 402, 403, that is, a fast x-scanner 402 and a fast y-scanner 403. One of these scanners 401, 402, 403 may be a resonant scanner, the other must be able to the synchronized to its resonant frequency.

The scan pattern results from the placement of the scan lines 5 of the individual strokes 7 next to each other. This is effected by a slow scanning movement by use of the slow deflection system or scanning system, 411, 412, 413, which contains a slow x-scanner, a slow y-scanner and a slow z-scanner, with which the optical system 2, 200 itself is moved. By a combination of slow scanning movement and fast oscillatory movement, the center position of the oscillatory movement is displaced slowly in an arbitrary desired direction in the processing volume 300.

Figure 8C:
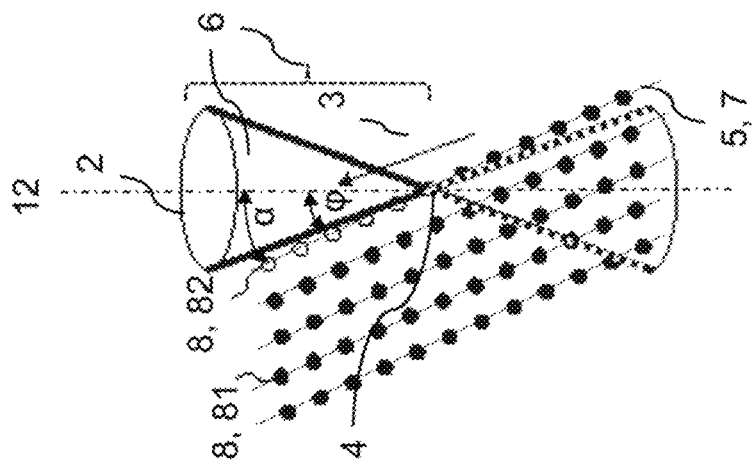
FIGS. 8a to 8c: the position of the focal cone of a focus effective zone to be realized to focus effective zones that are already realized for different scan patterns.
Figure 8B:
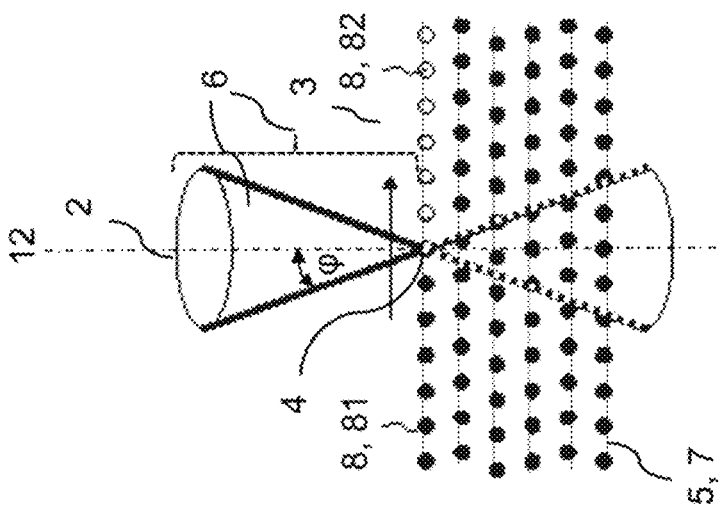
Figure 8A:
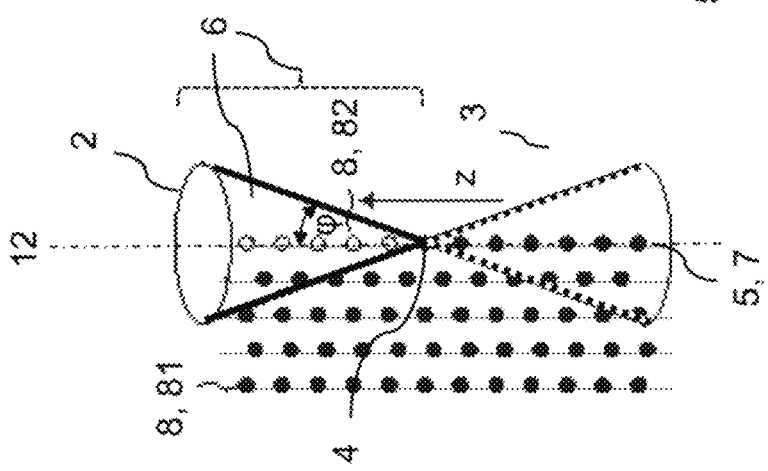

FIGS. 8a to 8c illustrate the different situations for the position of the focal cone 6 of a focused laser radiation to be realized for a laser focus effective zone 8, 82 to the laser focus effective zones 8, 81 already realized in different scan patterns. The focal cone 6 is understood to mean only the part visually marked with a bracket in these figures, not the other cone, which results in the beam direction behind the laser focus effective zone 8, 81, 82 by the "divergence" of the radiation.

In FIG. 8a, in which the laser focus effective zones 8, as already shown in the prior art and FIG. 1b, are placed along a vertical scan line 5, the scan pattern is thus constructed in columns, the focal cone 6 of yet to be realized laser focus effective zones 8, 82 projects into laser focus effective zones 8, 81 that are already realized of the strokes 7 that are already realized and thereby leads to shadowing.

Laser focus effective zones 8, 81 that are already realized should therefore not be in the focal cone 6 of the laser focus 4 for the laser focus effective zones 8, 82 still to be realized. With a line-by-line construction of the scan pattern, starting with the bottom line as shown in FIG. 8b, this is always given. However, a shadowing problem by laser focus effective zones 8, 81 already realized occurs then at least in the edge regions of a partial area already generated 11 to a next partial area of a processing area 11 to be generated—as already described above.

By an inclination of the scan lines 5 and thus of the strokes 7 such that the inclination angle α of the strokes 7 to the beam axis 12 is larger than the focal angle φ, that is, the angle between a straight line extending on the cone surface of the focal cone 6 and the beam axis 12, and such a sequence of the individual strokes 7, an inclined stroke 7 still to be realized is generated in the positive z-direction, thus against the beam direction of the focused radiation above an inclined stroke 7 already realized, as shown in FIG. 8c, any shadowing effect of laser focus effective zones 8, 81 already realized for laser focus effective zones 8, 82 still to be realized is avoided. With an appropriate inclination angle α of the strokes 7 or the scan line 5 on which the stroke 7 shall be realized, the placement of the laser focus 4 at an arbitrary location of the scan line 5 of the stroke 7 to be realized is possible in such a manner that the scan line 5 penetrates the focal cone 6 of the laser radiation only in the focal point 4. The scan pattern of FIG. 8c may be generated as shown in detail in FIG. 10.

FIG. 9 shows the advantageous side-by-side placement of inclined strokes 7 for processing a closed, cylindrical area 11. Therein, the strokes 7 are placed side-by-side such that existing strokes 7 from the part of the scan pattern already realized do not penetrate the focal cone 6 of the laser radiation, but only the diverging further cone in regions behind the laser focus 4. The processing of the area 11 is therefore not obstructed by shadowings generated by existing strokes 7.

In order to be able to close the area 11, without laser focus effective zones 8, 81 already realized reaching into the focal cone 6 of the focus 4 for laser focus effective zones 8, 82 still to be realized, the first strokes 7 should be encoded as shown in the region 22 of FIG. 9. A line 23 passing the starting points of the first side-by-side realized strokes 7 with a distance 10 to each other should form an angle α with a straight line in the z-direction, which is parallel to the base position beam axis 12, which angle is larger than the focal angle φ. In order to finally close the area 11, these first strokes 7 of the region 22 are respectively prolonged by a second stroke 7 so that the desired total height in the z-direction is reached.

The inclined strokes 7 or the inclined scan lines 5 with an inclination angle α which is larger than the focal angle φ, have a sufficiently large z-dimension despite their inclination for efficient filling of the processing area 11 with the laser focus effective zones 8.

In the following, the generation of an inclined scan line 5 and inclined strokes 7 is now described by synchronous change-of-direction-movements, in particular by synchronous oscillatory movements, of a fast z-scanner 401 and at least one of the fast lateral scanners 402, 403.

Figure 10:
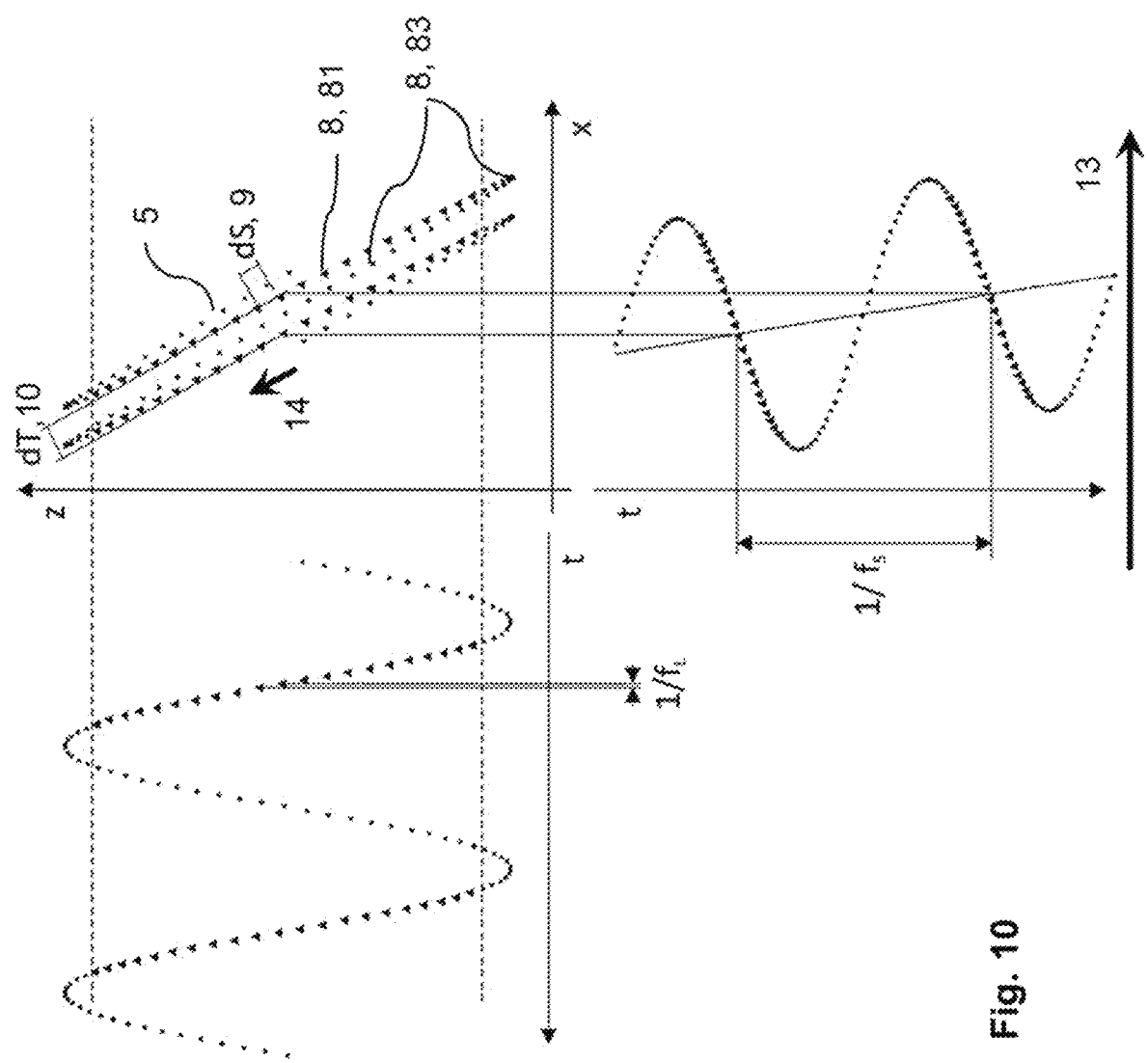
FIG. 10: the superposition of a sinusoidal oscillation of the fast z-scanner with a synchronous sinusoidal oscillation of a fast lateral scanner with slow change of the oscillation center point in the positive x-direction for generating straight strokes.

In FIG. 10, the superimposition of a sinusoidal oscillation of the fast z-scanner is initially shown with a synchronous sinusoidal oscillation of a fast lateral scanner in the x-direction with a slow change of the oscillation center point in the positive x-direction for generating straight strokes 7.

A sinusoidal oscillation of a fast z-scanner 401, which is shown in the z-t-diagram on the top left, is superimposed with a synchronous sinusoidal oscillation of a fast x-scanner 402 with a slow change of the oscillation center point, which is shown in the x-t-diagram on bottom right, to an inclined scan pattern as shown in the z-x-diagram top right. All points initially represent potential shooting positions of a short pulse laser used for this, because of its repetition rate, thus laser focus effective zones 8. The triangles thereby mark the actually realized, thus not blocked, laser focus effective zones 8, 81. In this case, the laser focus effective zones are only realized in the upward movement 14. Laser pulses at the reversal points of the sinusoidal movement and in the downward movement are masked.

The fast scanners for the z-direction and for the lateral spatial directions x- and/or y carry out synchronous sinusoidal oscillations without phase shift. An exact opposite phase oscillation can be realized by a negative amplitude. The path of the laser focus 4 then describes a total scanning line 5. If in addition a movement is carried out by the slow scanning system or the center of oscillation of the oscillation is changed slowly, the scan line 5 moves through the processing volume 300 during its generation and leaves a "wound" sinusoidal curve in the processing volume 300:

$$\vec{r}(t) = \begin{pmatrix} x(t) \\ y(t) \\ z(t) \end{pmatrix} = \begin{pmatrix} A_x \\ A_y \\ A_z \end{pmatrix} \sin(2\pi f_S t) + \begin{pmatrix} v_x \\ v_y \\ v_z \end{pmatrix} t + \begin{pmatrix} x_0 \\ y_0 \\ z_0 \end{pmatrix}$$

$f_s$ is the frequency of the sinusoidal oscillation of the scanner. The slow movement can locally be linearly approximated. The x-, y- and z-components of the current amplitude of the oscillation $A_x$, $A_y$, $A_z$, the x-, y- and z-components of the current speed of the slow scanning movement $v_x$, $v_y$, $v_z$, and the current position, thus the starting position in the space, $x_o$, $y_o$ and $z_o$ are, compared with the oscillation period of the fast scanners, so slowly temporally changeable that they can be assumed to be constant for a period of oscillation.

If the laser emits pulses with a fixed repetition rate, laser focus effective zones 8 with a spot-to-spot-distance, thus a distance of the two laser focus effective zones dS, 9 are generated in the space. The spot-to-spot-distances dS, 9 vary with the current position of the sinusoidal oscillation and are largest in the zero passage of the oscillation and almost zero in the reversing points.

A good approximation for dS is:

$$dS = \left\| \frac{dr}{dt} \right\| \cdot \frac{1}{f_L}$$

$f_L$ is the laser pulse repetition rate which is an integer part of the basic repetition rate of the laser. It is, depending on the duty cycle of the pulses every first, every second, every third pulse, etc. It is:

$$\frac{d\vec{r}(t)}{dt} = 2\pi f_S \begin{pmatrix} A_x \\ A_y \\ A_z \end{pmatrix} \cos(2\pi f_S t) + \begin{pmatrix} v_x \\ v_y \\ v_s \end{pmatrix}$$

dS is in the zero transitions:

$$\overline{dS} = \frac{2\pi f_S}{f_L} \left\| \begin{pmatrix} A_x \\ A_y \\ A_z \end{pmatrix} \right\| + \left\| \begin{pmatrix} v_x \\ v_y \\ v_s \end{pmatrix} \right\|.$$

By masking the laser pulses, and thus the laser focus effective zones 8, 83, in the reversal points, an excessive variation of the spot-to-spot-distances dS, 9, and in particular the realization of laser focus effective zones in a too large proximity to each other can be avoided. For example, the laser pulses can be masked when the distance between two laser focus effective zones, thus the spot-to-spot-distance dS, has fallen to about half of the value at the zero transition, thus when:

$$\cos(2\pi f_s t) = \pm 1/2.$$

The "hatching width" as the actual height of the strokes 7, thus the part of the scan line, on which laser focus effective zones 8 were or are realized are, is then $$2 \sin\left(\arccos \frac{1}{2}\right) = \sqrt{3} = 1.73$$

thus, 1.73 times of the amplitude of the oscillation A:

$$A = \left\| \begin{pmatrix} A_x \\ A_y \\ A_z \end{pmatrix} \right\|.$$

The distance between two adjacent "hatching" lines dT, 10 and thus two strokes 7 is, in the case, that cuts are only carried out in one oscillation direction, that is upwards 14 or downwards 15, is constant over an oscillation:

$$dT = \frac{v}{f_L} = \frac{1}{f_L} \left\| \begin{pmatrix} v_x \\ v_y \\ v_z \end{pmatrix} \right\|.$$

Figure 11:
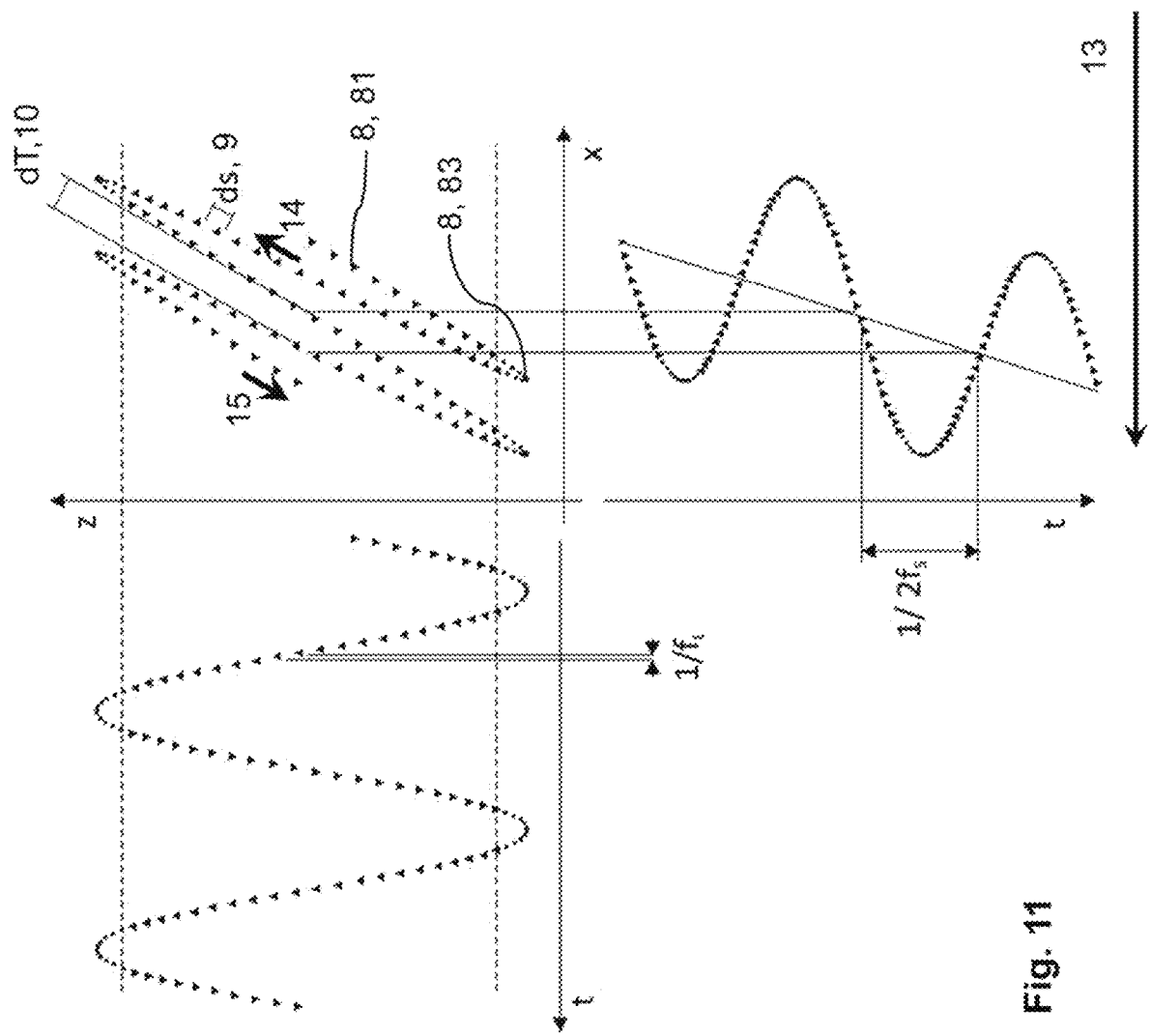
FIG. 11: the superposition of a sinusoidal oscillation of the fast z-scanner with a synchronous sinusoidal oscillation of a fast lateral scanner with slow change of the oscillation center point in the negative x-direction for the bidirectional generation of strokes.

FIG. 11 shows the superposition of a sinusoidal oscillation of the fast z-scanner with a synchronous sinusoidal oscillation of a fast lateral scanner in the x-direction with a slow change of the oscillation center point in the negative x-direction for the bidirectional generation of strokes 7.

In contrast to the example of FIG. 10, the strokes are generated here 7 on an inclined scan line 5 with a bidirectional laser incision in both the upward movement 14 and in the downward movement 15, see strokes 7 with upward pointing triangles for the upward movement and strokes 7 with downward pointing triangles for the downward movement in order to mark the corresponding laser focus effective zones 8.

In the bidirectional incision mode, the distance between two strokes dT, 10 also varies with the respective position on the scan line 5, but is half as large in the zero transitions as with the unidirectional incision mode of FIG. 10. If, as in the unidirectional case, one cuts at √3/2 of the amplitude, with which the distance between two laser focus effective zones dS falls to half of the maximum value at the zero transition, the line spacing and thus the distance dT, 10 of two strokes 7 alternately varies from 1/3 and to 5/3 of the value in the zero transition. The distance 2dT to the second nearest straight scan line 5, and thus to the second nearest stroke 5, remains constant 6/3 as in the unidirectional mode.

If the strokes 7 are to be introduced such that subsequent strokes still to be realized are arranged "over" the previously realized strokes 7, so that strokes 7 already realized do not shadow the focal cone 6 of the laser focus 4, the lateral oscillation, must be carried out in phase opposition to the z-oscillation for a positive slow movement in the x-direction as shown in FIG. 10, and the fast lateral oscillation in the x-direction must be carried out in phase to the fast z-oscillation for a negative movement in x-direction as shown in FIG. 11.

If a capsulotomy incision shall be carried out, there is the objective to generate an incision area 11 that cuts through the anterior skin of the lens of an eye, the so-called "anterior capsule" in a selectable hole geometry. This geometry can for example be elliptical or circular. The incision area 11 shall thereby extend with a minimum distance above and below the capsular bag, in order to ensure a safe cut.

Figure 12:
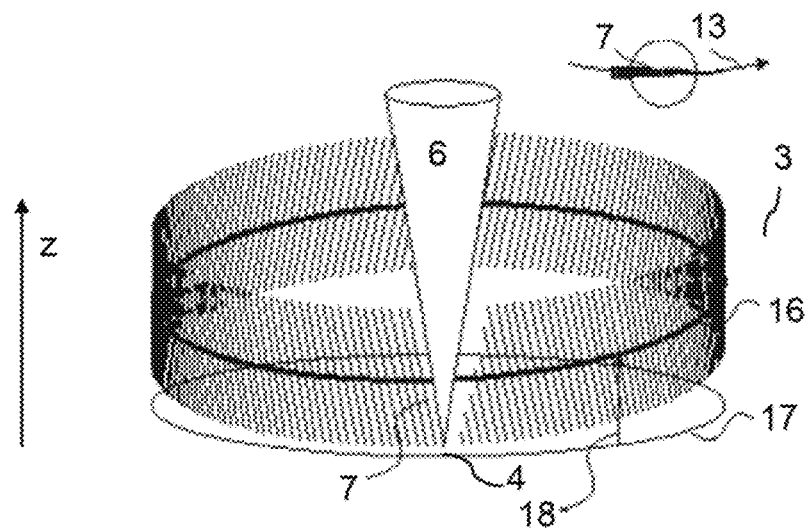
FIG. 12: a first scan pattern for generating a capsulotomy incision.

For executing such an incision, there are different possible scan patterns for the focus 4 of a pulsed laser beam, which is used for "cutting". A first possibility is shown in FIG. 12. FIG. 12 shows a first scan pattern for generating a capsulotomy incision, in which the slow movement follows laterally the hole geometry 17 and follows the z-height 18 of the capsular bag in the z-direction.

A fast oscillatory scanning movement in the z-direction is synchronized with fast oscillatory scanning movements tangentially to the lateral slow scanning movement 13, thus straight to the lateral component of the slow scanning movement 13, for forming the strokes 7, thus the laser focus effective zones 8 realized on a scan line 5 in the same direction. These effect therein a separation of the eye material 3 by photo disruption and thus contribute to the formation of an incision area 11. The image of a "lattice fence" inclined in the "fence direction" results.

At the top right in FIG. 12, a schematic diagram in plan view shows that the strokes 7 are aligned in the direction of progress of the slow scanning movement 13. The lower end of such a stroke 7 which is drawn thin, precedes the slow movement 13, the upper end, which is drawn thick, remains behind the slow movement 13, so that the focal cone 6 of the laser focus 4 for the laser focus effective zones 8 of the subsequent stroke 7 is never shadowed by strokes 7 already realized. At the point where the end of the incision area 11 shall meet again the starting point, the strokes 7 are limited at the beginning in such a manner that a V-shaped region remains free for forming the last strokes 7, which then fill up the initially incomplete strokes 7.

Figure 13:
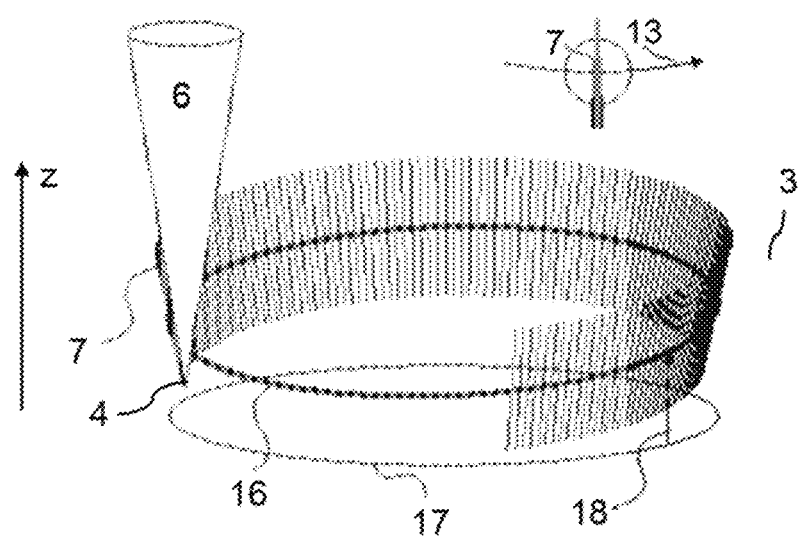
FIG. 13: a second scan pattern for generating a capsulotomy incision.

FIG. 13 shows a second scan pattern for generating a capsulotomy incision, in which the slow movement follows laterally along the hole geometry 17 and in the z-direction of the z-height 18 of the capsular bag.

A fast oscillatory scanning movement in the z-direction is synchronized to a lateral fast oscillatory scanning movement normal to the lateral slow scanning movement 13, that is, perpendicular to the lateral component of the slow scanning movement 13, for forming the strokes 7, that means the laser focus effective zones 8 realized on a scan line 5 in the same direction. These also effect a separation of the eye material 3 by photo disruption and thus contribute to the formation of an incision area 11. The image of an outwardly inclined "lattice fence" results thereof.

The top right in FIG. 13 shows a schematic diagram in plan view, in that the strokes 7 are aligned vertically to the advancement of the slow scanning movement 13. They always spare the zone for the focal cone 6 of the laser focus 4 for the subsequent stroke 7 free, regardless if the stroke 7 of the slow scanning movement 13 points up in the inside or outside area, as long as the condition that the angle of inclination α of the stroke 7 is larger than the focal angle φ of the focal cone 6 of the laser focus 4, described in FIG. 8*c*, is realized.

Figure 14:
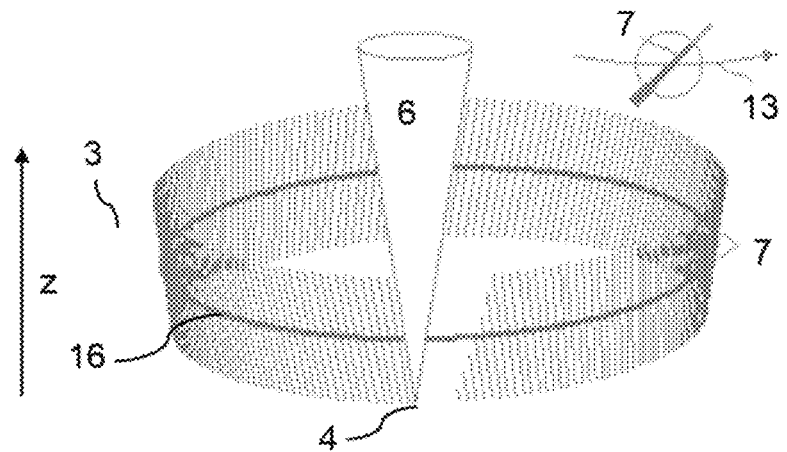
FIG. 14: a third scan pattern for generating a capsulotomy incision.

FIG. 14 shows a third scan pattern for generating a capsulotomy incision. A fast oscillatory scanning movement in the z-direction is synchronized to a lateral fast oscillatory scanning movement, which is carried out to the lateral slow scanning movement 13 at an angle between the tangential and the normal direction. This leads to the formation of the strokes 7, which also cause a separation of the eye material 3 by photo disruption and thus contribute to the formation of an incision area 11. Thus, an image similar to obliquely outwardly inclined but not fallen "pick-a-stick" game pieces results.

The top right in FIG. 14 shows a schematic diagram in plan view, in that the strokes 7 are aligned at an angle between the tangential and normal alignment to the progress of the slow scanning movement 13. The part of the strokes 7 preceding the slow scanning movement 13 which is drawn thin, is the end lower end of the strokes 7, and the thick-drawn part, which remains behind the slow scanning movement 13, is the upper end of the strokes 7. Thereby, the focal cone 6 of the laser focus 4 for the subsequent stroke 7 is not shadowed by stroke 7 already realized, provided that the condition is fulfilled that the angle of inclination α of the strokes 7 is larger than the focal angle φ of the focal cone 6 of the laser focus 4.

The scan pattern of FIG. 12 is the preferred example scan pattern for generating a capsulotomy incision. The hole geometry 17 essentially remains the same even if the capsular bag to be cut is no longer situated exactly at the planned position at the time of the incision, which might happen due to inaccuracies of measurement or a subsequent movement of the eye media, while with the scan patterns of FIGS. 13 and 14, the diameter of the capsulotomy incision actually realized depends on the actual z-position of the overlap of the incision area 11 with the capsular bag, thus a transparent eye material 3.

In practice, the scan pattern of FIG. 12 is also the one with the highest incision efficiency, thus the highest incision performance with the smallest laser energies and/or with the largest distances 9 of two laser focus effective areas 8.

Figure 15A:
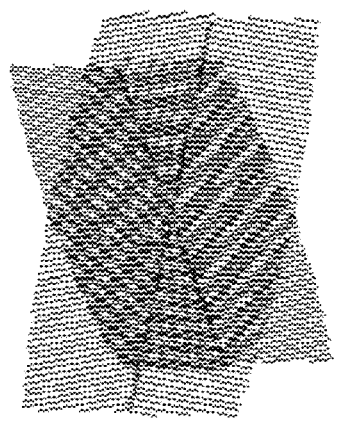
FIGS. 15a to 15c: different phases of a scan pattern for generating a lens fragmentation incision, FIGS. 15d and 15e an advantageous scan pattern with crossed incision planes.
Figure 15B:
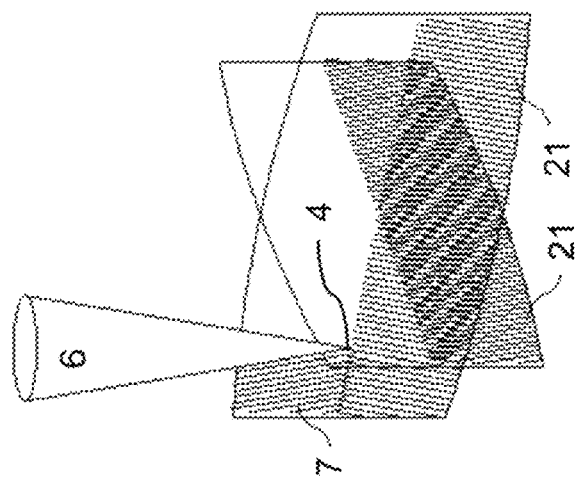
Figure 15C:
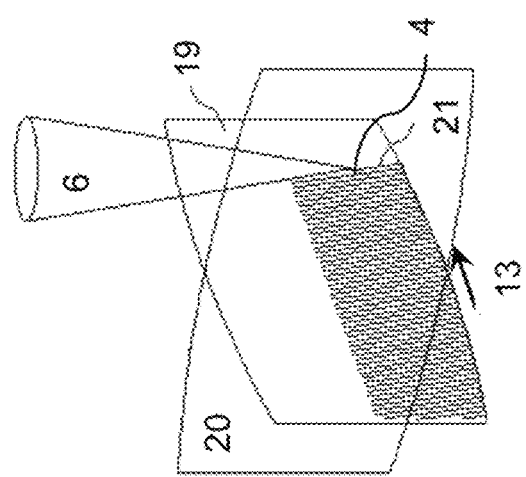
Figure 15D:
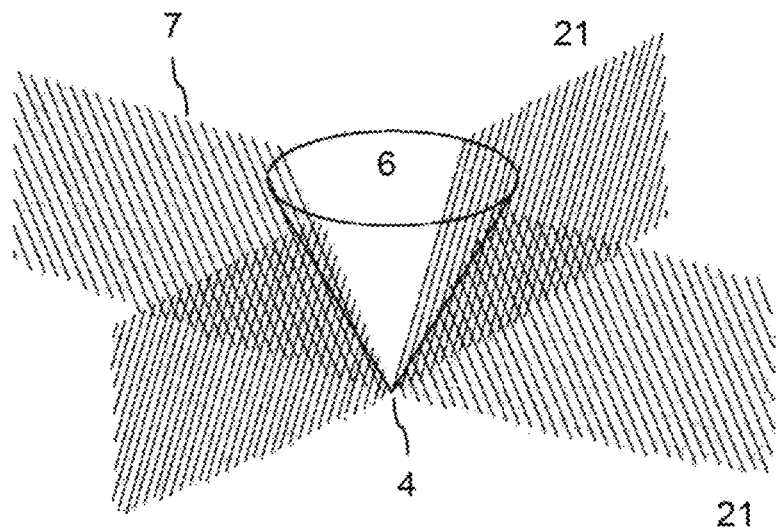
Figure 15E:
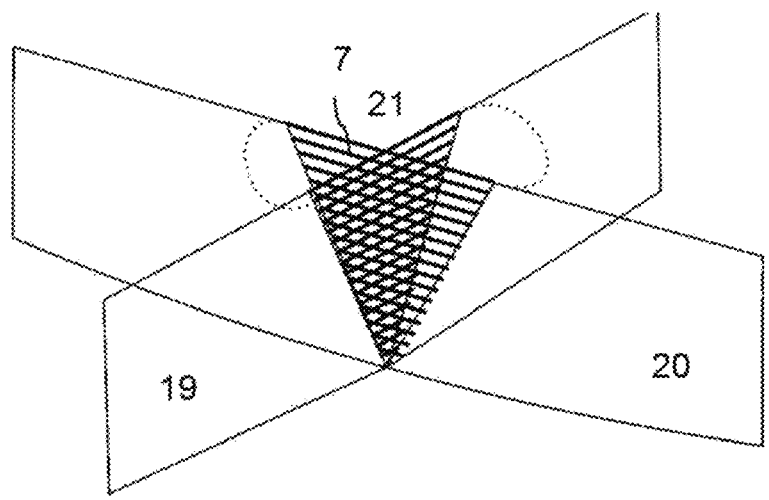

FIGS. 15*a* to 15*c* show various stages of a scan pattern for generating a lens fragmentation incision that again results from photo disruption using a pulsed laser beam. FIGS. 15*d* and 15*e* show a further solution for a corresponding scan pattern for completing the incision planes at crossing points.

The pulsed laser beam is usually realized here as for many other ophthalmologic purposes, too, with a femtosecond laser. Ideally, for the use for eye surgical purposes here as well as in the examples of FIGS. 12, 13, 14, 16, 17 and 18 a system for processing an area 11 in a processing volume 300 of a transparent material 3, as described in FIG. 3, is used, thus, in particular a system which permits a fast scanning movement in any direction in a section 600 of the processing volume 300 independently of a slow scanning movement in any direction in the entire processing volume 300, wherein the section 600 of the fast scanning movements is moved by the slow scanning movement through the processing volume 300.

But it is also possible, with appropriate adjustments, for example to simulate the interaction of the fast scanning movement with a slow scanning movement, to transfer it to a single scanning system, if necessary with considerable loss of speed, and thus to use other systems, such as the system for processing an area 11 in a processing volume 300 of a transparent material 3, as described in FIG. 19.

For the lens fragmentation, an incision area 11 has to be generated that divides a lens of an eye along freely selectable incision planes 19, 20. The incision planes 19, 20 should thereby comply with minimum distances to the edges of the lens, thus follow the curvature of the limiting lens surfaces above and below.

For the formation of an extended incision area 11, which cuts through the entire volume of the lens, the stroke of a fast scanning movement, in particular the stroke determined by the amplitude of an oscillatory movement of a fast z-scanner, is not sufficient to divide the lens completely.

In this case, the total incision area must be composed of several single incision bands 21. If a complete incision plane 19, 20 shall be generated in a processing volume 300, whose form is thus relevant over the entire plane, unlike to capsulotomy, where only the penetration of the capsular bag is relevant, the individual strokes 7 and thus the scan lines have to be arranged in this incision region 11. The strokes 7 thus must be inevitably inclined in the direction of progress of the slow movement 13 or inclined against the direction of progress of the slow movement 13, that is, analogous to the first scan pattern of the capsulotomy.

Again, a part of the laser pulses is masked, in order to prevent damage by the realization of two laser focus effective zones in close proximity. The laser pulses are always masked, in addition to the reversal points of the fast oscillatory scanning movements which are carried out by the fast scanners, when the scan line leaves the intended incision region of the incision planes 19, 20 at full amplitude of the oscillation. In order to not shadowing a subsequent incision band 21 by an individual incision band 21, all deep-seated incision bands 21 are created first, before proceeding with higher-seated bands 21, as shown in FIG. 15b. Thus, there is a floor type configuration. The completed pattern of the entire incision area 11 can be seen in FIG. 15c. At the penetration points of two incision bands 21 there is also a shadowing of the subsequently realized incision band 21 by the already completed incision band 21. Here, a conical region can first be left blank at the penetration point, which can be filled up from the bottom upwards only using the fast scanner after completion of the complete "floor".

FIGS. 15d and 15e illustrate once more the problem occurring at intersection of two incision planes, as shown here for two crossed incision planes of a lens fragmentation incision, and show another solution for an appropriate scan pattern for completing the incision planes at intersections: After the crossing incision bands 21 were generated with a funnel-shaped recess at the crossing point, as shown in FIG. 15d, which corresponds to a focal cone 6 of the laser focus 4, the funnel is completed by a cross-cut band 21 in the tunnel-shaped recess, which is generated by fast lateral oscillatory scanning movements and a slow z-scanning movement, as becomes apparent from the FIG. 15e.

In FIGS. 15a to 15c, superimposed incision bands 21 are inclined in different directions. The inclination directions depend on the progress direction of the slow scanning movement 13. The progress directions of the slow scanning movement 13 selected in FIG. 15a to FIG. 15c are thereby not mandatory, but can usually be chosen freely, however, the presence of already realized incision bands 21 possibly leads to a preferred direction of the slow scanning movement 13 for an incision band 21 still to be realized. Superimposed incision bands 21, which are inclined in the same direction because they are cut in the same direction 13 are also within the scope of the invention.

Figure 16A:
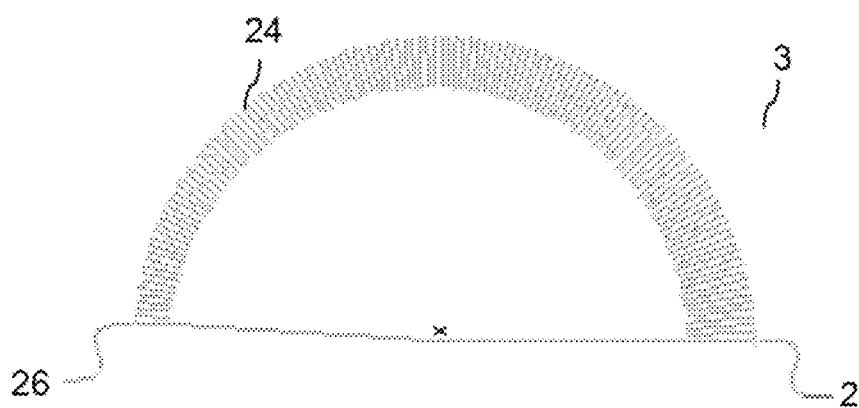
FIGS. 16a to 16c: a scan pattern for generating an arcuate incision in different views.
Figure 16B:
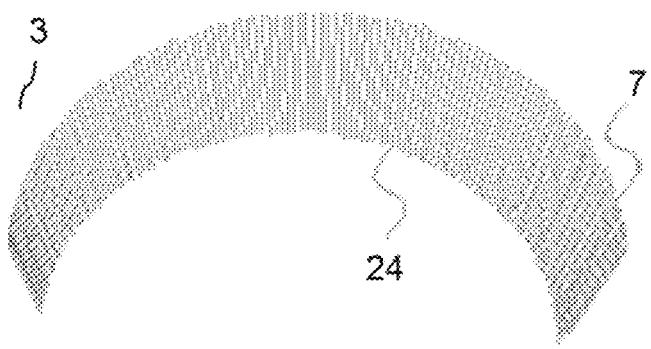
Figure 16C:
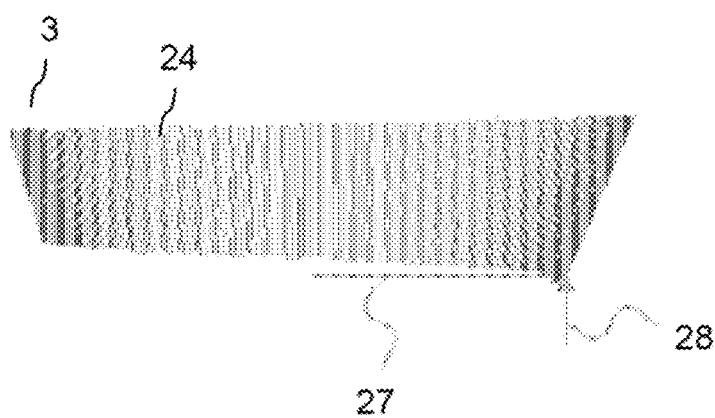

A scan pattern for generating an arcuate incision, that is an arcuate incision profile that can, for example, be used for the relaxation and correction of an astigmatism of an eye, is shown in FIGS. 16a to 16c in different views: FIG. 16a shows a plan view, FIG. 16b an oblique projection and FIG. 16c is a side view of a scan pattern and incision pattern, which is suitable for an arcuate incision.

For an arcuate incision an incision area in the form of a sloping, curved incision band 24 must be generated. This is solved in analogy to the scan patterns of FIGS. 13 and 14 for the capsulotomy, wherein the oblique position, that the inclination of each stroke 7, can be changed continuously, the start and end points, thus for example the height in the z-direction, at which the corresponding stroke 7 starts and ends, can be continuously varied, and starting angle and ending angle 26, 25 of the curved incision band 24 are freely selected.

The strokes 7 extend radially starting from an axis, as shown in the plan view of FIG. 16a.

The incision band 24 starts at a starting angle 25 and ends with an end angle 26. The start and end points of each stroke 7 at its respective angular position, for example, is given by the distance from the axis 27 and a z-height 28 and may change continually when passing through the angle range from the starting angle 25 to the end angle 26. Thus, the inclination, the length and the position of the strokes 7 can be adapted to the geometry of the eye tissue 3 to be cut. Since for this application, the incision band, or the incision area 24, unlike for the capsulotomy, shall be generated in the volume of the eye tissue, the free choice of the form of the incision area 24 is of high importance here.

A first and a second scan pattern for generating an access incision that is an access incision in the context of an ophthalmological treatment process is finally shown in different phases in FIGS. 17a to 17c and FIGS. 18a to 18c.

Such access incision or "access tunnel" shall be generated with a desired width, inclination and with appropriate "bending edges" for forming a self-sealing incision geometry passing the cornea of the eye 3.

Even if an access incision can be carried out with oblique strokes 7, it does not necessarily require a z-portion of the fast oscillatory scanning movement, since the scan vertical to the access direction 30 as shown in FIG. 17a, or parallel to the access direction 30 as shown in FIG. 18a can be carried out laterally in an x-y plane.

In some cases, the amplitude of the lateral oscillatory scanning movement is smaller than the required width of the tunnel. The incision area must then be dissected into sections 31, which are carried out sequentially.

In particular, the section 31 started in FIG. 17a reaches the maximum width of the oscillatory scanning movement at the end. In the phase of FIG. 17b, therefore, the tunnel is divided into two adjacent regions 31 and processed consecutively. A further subdivision, e.g. at bending edges 29, may be advantageous.

As shown in FIGS. 17c and 18c, the next plane is started only after completion of the flat region that has been processed in an x-y plane. The slow scanning system can thereby remain in a fixed position during the execution of the strokes 7 and only subsequently go to the next position after the completion of a section: The slow lateral scanner does not have to be used for a progression during the processing of an incision area: This can also be done by a slow zero position shift of the oscillation of the fast scanners.

When generating the inclined plane, the consideration of the size of the inclination angle compared to the focal angle is in turn necessary, in order to avoid shadowing effects. If necessary, it must also be filled obliquely here, as already suggested for FIGS. 14 and 15b and shown in FIG. 9.

Due to the slow movement of the oscillation center in the access direction, the individual strokes 7 are realized side by side. By masking the focus effective zones 8 of the laser pulses when the oscillation movement passes over the edges of the sections, the dimensional accuracy of the incision area 11, 31 is ensured with an arbitrarily chosen width course over the access direction 30.

FIG. 19 shows a second example of a system for processing an area in a processing volume of a transparent material by application of a focused radiation.

The system includes a device for generating a radiation 100 comprising a femtosecond laser with a wavelength in the range of 1020 nm to 1060 nm. The pulse duration of this femtosecond laser is between 500 fs to 600 fs, the pulse energy is about 10 µJ.

In addition, the system comprises an optical system 2, 200 for focusing the radiation in a focus 4, with a numerical aperture of 0.2, which has a field of view of about 6 mm. With this system, a processing volume 600 of 6 mm×6 mm×6 mm can be obtained.

The system shown here comprises a device for changing the position 400 of the focus 4 with a scanning system that can carry out scanning movements in the x-, y- and z-directions and may execute a scanning movement in any direction by the composition of these scanning movements. The device for changing the position 400 comprises three scanners 411, 412, 413, which possibly can displace the optics accordingly. However, since it comprises no second fast scanning system, which is independently adjustable from the first scanning system, the scan patterns presented here can be only be realized under loss of time in such a system.

Furthermore, the system comprises a one-piece central control system 500, which is connected to the device for generating a radiation 100, thus the femtosecond laser system, and connected with the device for changing the position 400 of the focus 4 via communication paths 501, and is configured to control the femtosecond laser system and all scanners 411, 412, 413 of the device for changing the position 400 of the focus 4.

Despite a lack of an additional fast scanning system, it is possible with such a scanning system to realize example scan patterns such that shadowing effects of the scan pattern already realized do not or minimally result for scan patterns still to be realized, when corresponding scan patterns are encoded in the control device 500 of this system. Thereby, working in a very limited local volume at any moment—as realized here—is advantageous in eye surgery, for example, to minimize the effects of a possible movement of the eye during the surgery in the eye tissue 3.

The control value for each scanning direction is thereby composed of slow, wide-ranging base components in the three spatial directions with arbitrary timing within these limits, and short-range, fast repetitive components corresponding to synchronous change-of-direction-movements in the three spatial directions and whose time course only slightly changes in each repetition.

The characteristics mentioned above and explained in various exemplary embodiments of the invention can thereby not only be applied in the combinations shown in the examples, but also in other combinations or alone, without leaving the scope of the present invention.

A description based on system characteristics applies with respect to these features analogously to the corresponding method, while method characteristics represent corresponding functional characteristics of the described system.

The invention claimed is:

1. An ophthalmologic therapy system for processing portion of a processing volume of a transparent material of an eye by application of focused radiation, comprising
   a device that generates radiation,
   an optical system that focuses the radiation at a focus in the processing volume, wherein the focus of the focused radiation has a focal angle ($\varphi$) and the focused radiation has a beam axis,
   a device that changes position of the focus in the processing volume, which can be described with three spatial directions x, y and z, wherein the z-direction proceeds parallel to a base position beam axis of the focused radiation,
   a control device that controls the ophthalmologic therapy system,
   wherein the device for changing the position of the focus comprises a first scanner that is a slow scanner adapted to perform a slow scanning movement three dimensionally in the three spatial directions in the processing volume of the transparent material and a second scanner that is a fast scanner adapted to perform a fast scanning movement three dimensionally in the three spatial directions, and independently from the slow scanning movement of the slow scanner in a section of the processing volume,
   wherein the section of the fast scanning movement is movable by the slow scanning movement in the entire processing volume.

2. The ophthalmologic therapy system according to claim 1, wherein the device that generates radiation further comprises a laser.

3. The ophthalmologic therapy system according to claim 2, wherein the laser further comprises a pulsed laser.

4. The ophthalmologic therapy system according to claim 1, wherein a scan pattern is encoded into the control device, the scan pattern comprising a sequence of focus effective zones of the focused radiation along a scan line in the processing volume, such that focus effective zones that have already been realized are always arranged outside of a focal cone which is formed by the focus of the focused radiation and the focal angle ($\varphi$), for yet to be implemented focus effective zones.

5. The ophthalmologic therapy system according to claim 1, wherein the second scanner further comprises a fast z-scanner and at least a fast lateral scanner that enables the fast scanning movement in the section of the processing volume in addition to the first scanner which comprises a slow z-scanner and at least one slow lateral scanner that enables the slow scanning movement in the processing volume.

6. The ophthalmologic therapy system according to claim 5, wherein the fast lateral scanner comprises a fast x-scanner and a fast y-scanner, or the fast lateral scanner comprises a fast R-scanner whose scanning movement can be oriented in an x-y-plane perpendicular to the base position beam axis by rotating about a rotation axis parallel to the base position beam axis.

7. The ophthalmologic therapy system according to claim 5, further comprising a fast z-scanner comprising a lens element oscillating in the z-direction, a fast lateral scanner, which comprises an x-y-mirror element movable around two axes or two individual mirror elements each respectively movable about one individual axis, a slow z-scanner, which comprises a lens element that is movable in a user defined fashion in the z-direction and a slow lateral scanner comprising a focus optical system movable in a user defined fashion in the lateral plane.

8. The ophthalmologic therapy system according to claim 5, adapted for executing a fast scanning movement by synchronous changes of direction of at least the fast z scanner and the fast lateral scanner.

9. The ophthalmologic therapy system according to claim 8, further adapted for executing synchronous oscillatory movements of at least two of the fast scanners.

10. The ophthalmologic therapy system according to claim 8, wherein one of the at least two fast scanners is a resonant scanner with a free oscillation, and all other of the at least two fast scanners are synchronized to the resonant scanner.

11. The ophthalmologic therapy system according to claim 8, further wherein the fast z-scanner and the at least one fast lateral scanner are adapted for synchronous oscillatory movements.

12. The ophthalmologic therapy system according to claim 11, wherein the slow scanning movement comprises a lateral component in the x-direction, in the y-direction or in both the x and y directions, and wherein the oscillating movements of the fast z-scanner and the at least one fast lateral scanner are synchronized such that
with a positive lateral component of the slow scanning movement in the x-direction, in the y-direction or in both the x and y directions, the oscillatory movements of the at least one fast lateral scanner, are in phase opposition to the oscillatory movement of the fast z-scanner, and such that
with a negative lateral component of the slow scanning movement in the x-direction, in the y-direction or in both the x and y directions, the oscillatory movements of the at least one fast lateral scanner, are in phase to the oscillatory movement of the fast z-scanner.

13. The ophthalmologic therapy system according to claim 4, further comprising a control device, in which a scan pattern is encoded, which has adjacent strokes with angles of inclination ($\alpha$) to the beam axis, wherein a stroke comprises a straight part of a scan line and is formed by stringing together focus effective zones of the focused radiation, and wherein the angle of inclination ($\alpha$) of the strokes to the beam axis are always larger or equal to the focal angle ($\varphi$) of the focused radiation.

14. The ophthalmologic therapy system according to claim 13, the encoding of the scan patterns in the control device further being such that the formation of the strokes through stringing together focus effective zones of the focused radiation is always formed in an upward movement or always in a downward movement or alternatively in an upward movement and in a downward movement implemented along the scan line.

15. The ophthalmologic therapy system according to claim 1, wherein the device that generates the radiation comprises a pulsed laser having a laser pulse repetition rate ($F_L$), and wherein a distance of focus effective zones from a preceding focus effective zone is determined through the laser pulse repetition rate ($F_L$) and an overall scanning speed, which is comprised of the scanning speeds of slow and fast scanning movements, wherein the control device, is further structured to mask a laser pulse, when a distance of the laser pulse's focus effective zone to a preceding focus effective zone falls below a minimum distance.

16. A method for processing a portion of a processing volume of a transparent material of an eye by application of focused radiation by application of an ophthalmologic therapy system which comprises
a device that generates the focused radiation; and
an optical system that focuses the radiation at a focus in the processing volume which can be described with three spatial directions x, y and z, wherein the focus of the focused radiation comprises a focal angle and the focused radiation comprises a beam axis;

the method comprising:
changing a position of the focus by a three dimensional slow scanning movement of a first scanner in the processing volume of the transparent material and a three dimensional fast scanning movement of a second scanner which is independent of the three dimensional slow scanning movement of the first scanner in a section of the processing volume determined by the three spatial directions; and
moving the section of the three dimensional fast scanning movement by the three dimensional slow scanning movement in the entire processing volume.

17. The method according to claim 16, further comprising carrying out the three dimensional fast scanning movement by synchronous changes of direction in at least two spatial directions.

18. The method according to claim 16, further comprising carrying out the three dimensional fast scanning movement, by synchronous oscillatory movements in at least two spatial directions.

19. The method according to claim 16, further comprising carrying out the three dimensional fast scanning movement by synchronous oscillatory movements in z-direction and in at least one of the two lateral spatial directions.

20. The method according to claim 17, further comprising carrying out the three dimensional slow scanning movement with a lateral component in the x-direction, in the y-direction or in both the x-direction and the y-direction, and synchronizing the fast oscillatory movements in the z-direction and in the x-direction, in the y-direction or in both the x-direction and the y-direction to one another such that, with a positive lateral component of the slow scanning movement in the x-direction, in the y-direction or in both the x-direction and the y-direction, the fast oscillatory movements in the x-direction, in the y-direction or in both the x-direction and the y-direction is carried out in phase opposition to the oscillatory movement in the z-direction, and such that, with a negative lateral component of the slow scanning movement in the x-direction, in the y-direction or in both the x-direction and the y-direction, the fast oscillatory movements in the x-direction, in the y-direction or in both the x-direction and the y-direction is carried out in phase to the oscillatory movement in the z-direction.

21. The method according to claim 16, further comprising generating a scan pattern which has mutually adjacent strokes with angles of inclination ($\alpha$) to the beam axis, wherein a stroke comprises a straight section of a scan line and is formed by stringing together focus effective zones of the focused radiation, wherein the angle of inclination ($\alpha$) of the strokes to the beam axis is larger or equal to a focal angle ($\varphi$) of the focused radiation.

22. The method according to claim 16, in which the device for generating radiation generates pulsed laser radiation with a laser pulse repetition rate ($f_L$), and further comprising determining a distance of a focus effective zone by a preceding focus effective zones by the laser pulse repetition rate ($F_L$) and an overall scanning speed, which is comprised of the scanning speeds of the slow and fast scanning movements, and masking a laser pulse when its focus effective zone falls below a set minimum distance to the preceding focus effective zone.

* * * * *